United States Patent
Knopf et al.

(10) Patent No.: US 9,526,759 B2
(45) Date of Patent: Dec. 27, 2016

(54) ACTIVIN-ACTRIIA ANTAGONISTS AND USES FOR TREATING OR PREVENTING BREAST CANCER

(75) Inventors: John Knopf, Carlisle, MA (US); Jasbir Seehra, Lexington, MA (US); Ravindra Kumar, Acton, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 1229 days.

(21) Appl. No.: 12/012,510

(22) Filed: Feb. 1, 2008

(65) Prior Publication Data

US 2009/0074768 A1 Mar. 19, 2009

Related U.S. Application Data

(60) Provisional application No. 60/899,070, filed on Feb. 1, 2007, provisional application No. 61/000,540, filed on Oct. 25, 2007.

(51) Int. Cl.

| *A61K 6/00* | (2006.01) |
|---|---|
| *A61K 38/00* | (2006.01) |
| *A61K 38/04* | (2006.01) |
| *A61K 38/16* | (2006.01) |
| *C07K 14/00* | (2006.01) |
| *C07K 14/435* | (2006.01) |
| *C07K 14/705* | (2006.01) |
| *A61K 38/17* | (2006.01) |
| *G01N 33/50* | (2006.01) |
| *G01N 33/573* | (2006.01) |
| *G01N 33/574* | (2006.01) |
| *C12N 9/12* | (2006.01) |

(52) U.S. Cl.
CPC .......... *A61K 38/1796* (2013.01); *A61K 38/179* (2013.01); *C07K 14/705* (2013.01); *C12N 9/12* (2013.01); *C12Y 207/1103* (2013.01); *G01N 33/5011* (2013.01); *G01N 33/573* (2013.01); *G01N 33/57415* (2013.01); *C07K 2319/30* (2013.01); *C07K 2319/32* (2013.01); *G01N 2333/91205* (2013.01)

(58) Field of Classification Search
CPC .......... A61K 6/00; A61K 38/00; A61K 38/04; A61K 38/16; A61K 38/17; A61K 38/177; A61K 38/179; C07K 1/00; C07K 14/00; C07K 14/435; C07K 14/705; C07K 2316/00; C07K 2319/00; C07K 2319/20; C07K 2319/30; C07K 2319/32

See application file for complete search history.

(56) References Cited

U.S. PATENT DOCUMENTS

| 4,973,577 A | 11/1990 | Vale, Jr. et al. |
|---|---|---|
| 5,118,667 A | 6/1992 | Adams et al. |
| 5,658,876 A | 8/1997 | Crowley et al. |
| 5,703,043 A | 12/1997 | Celeste et al. |
| 5,760,010 A | 6/1998 | Klein |
| 5,808,007 A | 9/1998 | Lee et al. |
| 5,824,637 A | 10/1998 | Crowley et al. |
| 5,847,078 A | 12/1998 | Eto et al. |
| 5,885,794 A | 3/1999 | Mathews et al. |
| 6,004,780 A | 12/1999 | Soppet et al. |
| 6,034,062 A | 3/2000 | Thies et al. |
| 6,093,547 A | 7/2000 | Jin et al. |
| 6,132,988 A | 10/2000 | Sugino et al. |
| 6,162,896 A | 12/2000 | Mathews et al. |
| 6,287,816 B1 | 9/2001 | Rosen et al. |
| 6,440,930 B1 | 8/2002 | Rinella, Jr. |
| 6,451,334 B2 | 9/2002 | Perrine |
| 6,537,966 B1 | 3/2003 | Duan et al. |
| 6,548,634 B1 | 4/2003 | Ballinger et al. |
| 6,599,876 B2 | 7/2003 | Kojima |
| 6,605,699 B1 | 8/2003 | Ni et al. |
| 6,632,180 B1 | 10/2003 | Laragh |
| 6,656,475 B1 | 12/2003 | Lee et al. |
| 6,656,708 B1 | 12/2003 | Yu et al. |
| 6,692,925 B1 * | 2/2004 | Miyazono et al. ............ 435/7.2 |
| 6,696,260 B1 | 2/2004 | Lee et al. |
| 6,777,205 B1 | 8/2004 | Carcagno et al. |
| 6,835,544 B2 | 12/2004 | Mathews et al. |
| 6,891,082 B2 | 5/2005 | Lee et al. |
| 6,914,128 B1 | 7/2005 | Salfeld et al. |
| 7,052,873 B2 | 5/2006 | Tsuchiya |
| 7,192,717 B2 | 3/2007 | Hill et al. |
| 7,202,210 B2 | 4/2007 | Wolfman et al. |
| 7,261,893 B2 | 8/2007 | Veldman et al. |
| 7,320,789 B2 | 1/2008 | Aghajanian et al. |
| 7,560,441 B2 | 7/2009 | Wolfman et al. |
| 7,612,041 B2 | 11/2009 | Knopf et al. |
| 7,709,605 B2 | 5/2010 | Knopf et al. |
| 7,842,663 B2 | 11/2010 | Knopf et al. |

(Continued)

FOREIGN PATENT DOCUMENTS

| EP | 1 174 149 | 1/2002 |
|---|---|---|
| EP | 1 416 273 A1 | 5/2004 |

(Continued)

OTHER PUBLICATIONS

Chamberlain et al. Expert Opinion on Pharmacotherapy 1(4): 603-614, 2000.*
Bodey et al. Anticancer Research 20: 2665-2676, 2000.*
Gura et al. Science 278: 1041 and 1042, Nov. 7, 1997.*
Binkert, et al., "Cloning, sequence analysis and expression of a cDNA encoding a novel insulin-like growth factor binding protein (IGFBP-2)," The EMBO Journal, 8(9):2497-2502 (1989).
Chapman, B., et al., "Effect of intron A from human cytomegalovirus (Towne) immediate-early gene on heterologous expression in mammalian cells," Nucleic Acids Research, 19(14):3979-3986 (1991).
Benny Klimek, Margaret E., et al., "Acute inhibition of myostatin-family proteins preserves skeletal muscle in mouse models of cancer cachexia," Biochemical and Biophysical Research Communications, 391:1548-1554 (2010).

(Continued)

*Primary Examiner* — Alana Harris Dent
(74) *Attorney, Agent, or Firm* — Ropes & Gray LLP

(57) ABSTRACT

In certain aspects, the present invention provides compositions and methods for treating or preventing breast cancer in humans.

34 Claims, 3 Drawing Sheets

(56) References Cited

U.S. PATENT DOCUMENTS

| | | |
|---|---|---|
| 7,893,213 B2 | 2/2011 | Mathews et al. |
| 7,919,296 B2 | 4/2011 | Wang |
| 7,947,646 B2 | 5/2011 | Sun et al. |
| 7,951,771 B2 | 5/2011 | Knopf et al. |
| 7,968,091 B2 | 6/2011 | Woolf et al. |
| 7,988,973 B2 | 8/2011 | Sherman |
| 8,007,809 B2 | 8/2011 | Sherman |
| 8,058,229 B2 | 11/2011 | Seehra et al. |
| 8,067,360 B2 | 11/2011 | Knopf et al. |
| 8,110,355 B2 | 2/2012 | Atwood et al. |
| 8,124,830 B2 | 2/2012 | Lee et al. |
| 8,128,933 B2 | 3/2012 | Knopf et al. |
| 8,138,142 B2 | 3/2012 | Seehra et al. |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,293,236 B2 | 10/2012 | Lin et al. |
| 8,293,881 B2 | 10/2012 | Seehra et al. |
| 8,309,082 B2 | 11/2012 | Han et al. |
| 8,343,933 B2 | 1/2013 | Knopf et al. |
| 8,388,968 B2 | 3/2013 | Berger et al. |
| 8,410,043 B2 | 4/2013 | Sun et al. |
| 8,435,948 B2 | 5/2013 | Zaidi et al. |
| 8,501,678 B2 | 8/2013 | Sun et al. |
| 8,629,109 B2 | 1/2014 | Knopf et al. |
| 8,637,023 B2 | 1/2014 | Lin et al. |
| 8,703,694 B2 | 4/2014 | Knopf et al. |
| 8,703,927 B2 | 4/2014 | Seehra et al. |
| 8,716,459 B2 | 5/2014 | Sun et al. |
| 8,753,627 B2 | 6/2014 | Han et al. |
| 8,765,663 B2 | 7/2014 | Seehra et al. |
| 8,822,411 B2 | 9/2014 | Lee et al. |
| 8,865,168 B2 | 10/2014 | Lin et al. |
| 8,895,016 B2 | 11/2014 | Sherman et al. |
| 8,987,203 B2 | 3/2015 | Van Leeuwen et al. |
| 8,999,917 B2 | 4/2015 | Sun et al. |
| 2001/0039036 A1 | 11/2001 | Matthews et al. |
| 2003/0082233 A1 | 5/2003 | Lyons et al. |
| 2003/0083251 A1 | 5/2003 | Westenfelder |
| 2003/0118556 A1 | 6/2003 | Kaspar et al. |
| 2003/0144203 A1 | 7/2003 | Bowen |
| 2003/0215913 A1 | 11/2003 | Alvarez et al. |
| 2003/0224397 A1 | 12/2003 | Lowman et al. |
| 2003/0224501 A1 | 12/2003 | Young et al. |
| 2004/0033511 A1 | 2/2004 | Pfizenmaier et al. |
| 2004/0132675 A1 | 7/2004 | Kuo et al. |
| 2004/0138129 A1 | 7/2004 | MacLeod |
| 2004/0197828 A1 | 10/2004 | Gaddy |
| 2004/0209805 A1 | 10/2004 | Phillips et al. |
| 2004/0223966 A1 | 11/2004 | Wolfman et al. |
| 2005/0106148 A1 | 5/2005 | Kay et al. |
| 2005/0197292 A1 | 9/2005 | Smithson et al. |
| 2005/0239070 A1 | 10/2005 | Von Knebel-Doeberitz et al. |
| 2005/0244867 A1 | 11/2005 | Soppet et al. |
| 2005/0257278 A1 | 11/2005 | Lee et al. |
| 2006/0068468 A1 | 3/2006 | Knopf et al. |
| 2006/0172347 A1 | 8/2006 | Mellor et al. |
| 2006/0210657 A1 | 9/2006 | Chou |
| 2007/0048830 A1 | 3/2007 | Gilbert et al. |
| 2007/0117130 A1 | 5/2007 | Han et al. |
| 2007/0149455 A1 | 6/2007 | Wolfman et al. |
| 2007/0172956 A1 | 7/2007 | Magari et al. |
| 2007/0184052 A1 | 8/2007 | Lin et al. |
| 2007/0249022 A1 | 10/2007 | Knopf et al. |
| 2007/0275895 A1 | 11/2007 | Duan et al. |
| 2007/0292885 A1 | 12/2007 | Bejanin et al. |
| 2008/0021104 A1 | 1/2008 | Tarallo |
| 2008/0075692 A1 | 3/2008 | Perrine |
| 2008/0089897 A1 | 4/2008 | Wolfman |
| 2008/0102065 A1 | 5/2008 | Borges et al. |
| 2008/0139590 A1 | 6/2008 | Qian et al. |
| 2008/0261879 A1 | 10/2008 | Melton et al. |
| 2009/0005308 A1 | 1/2009 | Knopf et al. |
| 2009/0017019 A1 | 1/2009 | Shields et al. |
| 2009/0047281 A1 | 2/2009 | Sherman |
| 2009/0074768 A1 | 3/2009 | Knopf et al. |
| 2009/0087433 A1 | 4/2009 | Wolfman et al. |
| 2009/0098113 A1 | 4/2009 | Knopf et al. |
| 2009/0099086 A1 | 4/2009 | Knopf et al. |
| 2009/0118188 A1 | 5/2009 | Knopf et al. |
| 2009/0142333 A1 | 6/2009 | Knopf et al. |
| 2009/0148436 A1 | 6/2009 | LaVallie et al. |
| 2009/0163417 A1* | 6/2009 | Sherman ............... 514/12 |
| 2009/0202471 A1 | 8/2009 | Khetani et al. |
| 2009/0226460 A1 | 9/2009 | Phillips et al. |
| 2010/0008918 A1 | 1/2010 | Sherman et al. |
| 2010/0015144 A1 | 1/2010 | Sherman et al. |
| 2010/0028331 A1 | 2/2010 | Sherman et al. |
| 2010/0028332 A1 | 2/2010 | Sherman et al. |
| 2010/0068215 A1 | 3/2010 | Seehra et al. |
| 2010/0113327 A1 | 5/2010 | Van Leeuwen et al. |
| 2010/0125099 A1 | 5/2010 | 't Hoen et al. |
| 2010/0183624 A1 | 7/2010 | Seehra et al. |
| 2010/0272734 A1 | 10/2010 | Berger et al. |
| 2010/0279409 A1 | 11/2010 | Robson et al. |
| 2010/0316644 A1 | 12/2010 | Seehra et al. |
| 2011/0038831 A1 | 2/2011 | Seehra et al. |
| 2011/0070233 A1 | 3/2011 | Seehra et al. |
| 2011/0092670 A1 | 4/2011 | Knopf et al. |
| 2011/0129469 A1 | 6/2011 | Koncarevic et al. |
| 2011/0135638 A1 | 6/2011 | Seehra et al. |
| 2011/0218147 A1 | 9/2011 | Knopf et al. |
| 2011/0286998 A1 | 11/2011 | Gregory et al. |
| 2011/0293526 A1 | 12/2011 | Plikus et al. |
| 2012/0003218 A1 | 1/2012 | Sherman et al. |
| 2012/0015877 A1 | 1/2012 | Seehra et al. |
| 2012/0052067 A1 | 3/2012 | Sherman |
| 2012/0148588 A1 | 6/2012 | Knopf et al. |
| 2012/0156204 A1 | 6/2012 | Seehra et al. |
| 2012/0232021 A1 | 9/2012 | Martini et al. |
| 2012/0237521 A1 | 9/2012 | Berger et al. |
| 2013/0004489 A1 | 1/2013 | Knopf et al. |
| 2013/0065299 A1 | 3/2013 | Knopf et al. |
| 2013/0071393 A1 | 3/2013 | Seehra et al. |
| 2013/0108650 A1 | 5/2013 | Kumar et al. |
| 2013/0177559 A1 | 7/2013 | Seehra et al. |
| 2013/0184210 A1 | 7/2013 | Knopf et al. |
| 2013/0195862 A1 | 8/2013 | Knopf et al. |
| 2013/0225484 A1 | 8/2013 | Sun et al. |
| 2013/0243743 A1 | 9/2013 | Seehra et al. |
| 2013/0244324 A1 | 9/2013 | Seehra et al. |
| 2013/0287765 A1 | 10/2013 | Zaidi et al. |
| 2013/0303068 A1 | 11/2013 | Hall et al. |
| 2013/0344091 A1 | 12/2013 | Berger et al. |
| 2014/0056902 A1 | 2/2014 | Shimizu et al. |
| 2014/0079700 A1 | 3/2014 | Knopf et al. |
| 2014/0194355 A1 | 7/2014 | Sun et al. |
| 2014/0220033 A1 | 8/2014 | Han et al. |
| 2014/0348827 A1 | 11/2014 | Sun et al. |
| 2015/0072927 A1 | 3/2015 | Lin et al. |
| 2015/0086556 A1 | 3/2015 | Han et al. |
| 2015/0111248 A1 | 4/2015 | Bancel et al. |
| 2015/0139983 A1 | 5/2015 | Karni et al. |
| 2015/0231206 A1 | 8/2015 | Sun et al. |
| 2015/0258120 A1 | 9/2015 | Zarnitsyn et al. |
| 2015/0266950 A1 | 9/2015 | Sung et al. |
| 2015/0276766 A1 | 10/2015 | Sung et al. |
| 2015/0283209 A1 | 10/2015 | Sung et al. |
| 2015/0328249 A1 | 11/2015 | Gonzalez-Cadavid et al. |

FOREIGN PATENT DOCUMENTS

| | | |
|---|---|---|
| EP | 1 362 062 | 5/2005 |
| JP | 2007-099764 | 4/2007 |
| WO | WO 92/04913 A1 | 4/1992 |
| WO | WO-92/20793 A1 | 11/1992 |
| WO | WO-93/00432 A1 | 1/1993 |
| WO | WO 94/15965 A1 | 7/1994 |
| WO | WO-94/26893 A1 | 11/1994 |
| WO | WO-9510611 A1 | 4/1995 |
| WO | WO-95/29685 A1 | 11/1995 |
| WO | WO 97/23613 A2 | 7/1997 |
| WO | WO-98/18926 A1 | 5/1998 |
| WO | WO-99/06559 A1 | 2/1999 |

(56) References Cited

FOREIGN PATENT DOCUMENTS

| | | |
|---|---|---|
| WO | WO 00/18932 A2 | 4/2000 |
| WO | WO-00/25807 A1 | 5/2000 |
| WO | WO-00/43781 | 7/2000 |
| WO | WO 00/62809 | 10/2000 |
| WO | WO-01/36001 | 5/2001 |
| WO | WO-01/43763 | 6/2001 |
| WO | WO-02/10214 A2 | 2/2002 |
| WO | WO-02/22680 | 3/2002 |
| WO | WO-02/36152 | 5/2002 |
| WO | WO-02/40501 A2 | 5/2002 |
| WO | WO-02/43759 A2 | 6/2002 |
| WO | WO-02074340 A1 | 9/2002 |
| WO | WO-02/085306 A2 | 10/2002 |
| WO | WO 02/094852 A2 | 11/2002 |
| WO | WO-03/006057 A1 | 1/2003 |
| WO | WO-03/053219 A2 | 7/2003 |
| WO | WO-03/072808 A1 | 9/2003 |
| WO | WO-03/087162 A2 | 10/2003 |
| WO | WO-2004/016639 A1 | 2/2004 |
| WO | WO-2004/039948 A1 | 5/2004 |
| WO | WO-2004/069237 A1 | 8/2004 |
| WO | WO-2004/086953 A2 | 10/2004 |
| WO | WO-2004/092199 A2 | 10/2004 |
| WO | WO-2004/108157 A2 | 12/2004 |
| WO | WO 2005/003158 A2 | 1/2005 |
| WO | WO-2005/009460 A2 | 2/2005 |
| WO | WO 2005/014650 A2 | 2/2005 |
| WO | WO-2005/028517 A2 | 3/2005 |
| WO | WO-2005/053795 A2 | 6/2005 |
| WO | WO 2005/070967 A2 | 8/2005 |
| WO | WO-2005/094871 A2 | 10/2005 |
| WO | WO-2005/097825 A2 | 10/2005 |
| WO | WO-2005/113590 A2 | 12/2005 |
| WO | WO-2006002387 A2 | 1/2006 |
| WO | WO-2006/012627 | 2/2006 |
| WO | WO 2006/020884 A2 | 2/2006 |
| WO | WO-2006/068468 | 3/2006 |
| WO | WO-2006/039400 A2 | 4/2006 |
| WO | WO-2006/083183 A1 | 8/2006 |
| WO | WO-2006/088972 A2 | 8/2006 |
| WO | WO-2006/115274 A1 | 11/2006 |
| WO | WO-2007/024715 A2 | 3/2007 |
| WO | WO 2007/038703 A2 | 4/2007 |
| WO | WO-2007/053775 A1 | 5/2007 |
| WO | WO-2007/062188 | 5/2007 |
| WO | WO-2007/067616 A2 | 6/2007 |
| WO | WO-2007/071023 | 6/2007 |
| WO | WO-2007/075702 | 7/2007 |
| WO | WO 2007/076127 A2 | 7/2007 |
| WO | WO-2007/087505 | 8/2007 |
| WO | WO-2007/101060 | 9/2007 |
| WO | WO-2008/015383 A2 | 2/2008 |
| WO | WO-2008031061 | 3/2008 |
| WO | WO-2008060139 | 5/2008 |
| WO | WO 2008/072723 A1 | 6/2008 |
| WO | WO-2008/073292 A2 | 6/2008 |
| WO | WO-2008/076437 | 6/2008 |
| WO | WO 2008/094708 A2 | 8/2008 |
| WO | WO-2008/097541 | 8/2008 |
| WO | WO-2008/100384 | 8/2008 |
| WO | WO-2008/109167 A2 | 9/2008 |
| WO | WO 2008/151078 A1 | 12/2008 |
| WO | WO 2009/009059 A1 | 1/2009 |
| WO | WO-2009/021747 | 2/2009 |
| WO | WO 2009/025651 A1 | 2/2009 |
| WO | WO-2009019504 A1 | 2/2009 |
| WO | WO-2009019505 A2 | 2/2009 |
| WO | WO-2009/070243 | 6/2009 |
| WO | WO-2009114180 A1 | 9/2009 |
| WO | WO 2009/137075 A1 | 11/2009 |
| WO | WO-2009137613 A2 | 11/2009 |
| WO | WO 2009/158015 A2 | 12/2009 |
| WO | WO 2009/158025 A2 | 12/2009 |
| WO | WO-2009/158033 A2 | 12/2009 |
| WO | WO 2010/019261 A1 | 2/2010 |
| WO | WO 2010/083034 A1 | 7/2010 |
| WO | WO-2010/125003 A1 | 11/2010 |
| WO | WO 2010/144452 | 12/2010 |
| WO | WO 2010/151426 | 12/2010 |
| WO | WO-2011/020045 | 2/2011 |
| WO | WO-2011/031901 A1 | 3/2011 |
| WO | WO-2012/027065 A2 | 3/2012 |
| WO | WO-2013006437 A1 | 1/2013 |
| WO | WO-2013/059347 A1 | 4/2013 |
| WO | WO-2013/063536 A1 | 5/2013 |
| WO | WO 2014/066487 A2 | 5/2014 |
| WO | WO-2014064292 A1 | 5/2014 |
| WO | WO-2014152940 A1 | 9/2014 |
| WO | WO-2015017576 A1 | 2/2015 |
| WO | WO-2015022658 A2 | 2/2015 |
| WO | WO-2015089575 A1 | 6/2015 |
| WO | WO-2015108972 A1 | 7/2015 |
| WO | WO-2015111008 A2 | 7/2015 |
| WO | WO-2015152183 A1 | 10/2015 |
| WO | WO-2015162590 A1 | 10/2015 |
| WO | WO-2015192127 A2 | 12/2015 |

OTHER PUBLICATIONS

Berenson, J.R., "Multiple Myeloma," Multiple Myeloma: Plasma Cell Disorders: Merck Manual Professional, pp. 1-5, Jul. 2008.

Cadena, S.M., et al., "Administration of a Soluble Activin Type IIB Receptor Promotes Skeletal Muscle Growth Independent of Fiber Type," Journal of Applied Physiology, 109:635-642 (2010).

Caricasole, A. A. D., et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).

Chamow, S.M., and Ashkenazi, A., "Immunoadhesins: Principles and Applications," TIBTECH, 14: 52-60 (1996).

Delogu, G., et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).

DePaolo, L.V., et al., "Passive Immunoneutralization with a Monoclonal Antibody Reveals a Role for Endogenous Activin-B in Mediating FSH Hypersecretion during Estrus and Following Ovariectomy of Hypophysectomized, Pituitary-Grafted Rats," Endocrinology, 130(3):1741-1743 (1992).

Gilchrist, A., et al., "Antagonists of the Receptor-G Protein Interface Block Gi-coupled Signal Transduction," Journal of Biological Chemistry, The American Society of Biological Chemists, Inc., 273(24):14912-14919 (1998).

Greenwald, et al., "Characterization of the Extracellular Ligand-Binding Domain of the Type II Activin Receptor," Biochemistry, 37(47):16711-16718 (1998).

Hsieh, Matthew M, et al., "HIF-prolyl hydroxylase inhibition results in endogenous erythropoietin induction, erythrocytosis, and modest fetal hemoglobin expression in rhesus macaques," Blood, 110(6):2140-2147 (2007).

Kumar, T.R., et al., "Regulation of FSHbβ and GnRH Receptor Gene Expression in Activin Receptor II Knockout Male Mice," Mol. Cell. Endocrinol., 212(1-2):19-27 (2003).

Lu, S., et al., "Simian Immunodeficiency Virus DNA Vaccine Trial in Macaques," Journal of Virology, 70(6):3978-3991 (1996).

Maguer-Satta, V., et al, "A Novel Role for Fibronectin Type 1 Domain in the Regulation of Human Hematopoietic Cell Adhesiveness Through Binding to Follistatin Domains of FLRG and Follistatin," Experimental Cell Research, Academic Press, 312(4):434-442 (2006).

Maguer-Satta, V., et al., "FLRG, Member of the Follistatin Family, a New Player in Hematopoiesis," Molecular and Cellular Endocrinology, Elsevier Ireland Ltd., 225(1-2):109-118 (2004).

Mathews, L.S., et al., "Expression Cloning of an Activin Receptor, a Predicted Transmembrane Serine Kinase," Cell, 65(6):973-982 (1991).

Matzuk et al., "Cloning of the human activin receptor cDNA reveals high evolutionary conservation," Biochim Biophys Acta, 1130(1):105-108 (1992).

(56) References Cited

OTHER PUBLICATIONS

McPherron, A.C., et al., "GDF-3 and GDF-9: Two New Members of the Transforming Growth Factor-B Superfamily Containing a Novel Pattern of Cysteines," Journal of Endocrinology, 268(5):3444-3449 (1993).
Murata, T., et al., "Anti Activin A Antibody (IgY) Specifically Neutralizes Various Activin A Activities," Proceedings of the Society for Experimental Biology & Medicine, 211(1):100-107 (1996).
Rosenzweig et al., "Cloning and characterization of a human type II receptor for bone morphogenetic proteins," PNAS, 92:7632-7636 (1995).
Ruckle et al., "Single-Dose, Randomized, Double-Blind, Placebo-Controlled Study of ACE-011 (ACTRIIA-IgG1) in Postmenopausal Women," Journal of Bone and Mineral Research, vol. 24(4), pp. 744-752 (2009).
Sako, D., et al., "Characterization of the Ligand Binding Functionality of the Extracellular Domain of Activin Receptor Type IIB," The Journal of Biological Chemistry, 285(27):21037-21048 (2010).
Schmelzer, C.H., et al., "Purification and Characterization of Recombinant Human Activin B," Biochimica et Biophysica Acta, 1039(2):135-141 (1990).
Thompson, T.B., et al., "Beta A versus beta B: is it merely a matter of express?," Molecular and Cellular Endocrinology, 225:9-17 (2004).
Tisdale, M.J., "Cachexia in Cancer Patients," Nat. Rev. Cancer, 2:862-871 (2002).
Ukkola, et al., "Adiponectin: A Link Between Excess Adiposity and Associated Comorbidities?", Journal of Molecular Medicine, 80(11):696-702 (2002).
Walsh, F. S, et al., "Myostatin: a modulator of skeletal-muscle stems cells," Biochemical Society Transactions, 33(Pt.6):1513-1517 (2005).
Wang, W., et al., "GDF-3 is an adipogenic cytokine under high fat dietary condition," Biochemical and Biophysical Research Comm., 321(4):1024-1031 (2004).
Ludlow, H., et al., "Development of a new antibody to the human inhibin/activin βB subunit and its application to improved inhibin B ELISAs," J. Immunol. Methods, 329:102-111 (2008).
Abrahams, B. and Ertel, S., 'Acceleron Pharma at Wells Fargo Healthcare Conference—Final', published on Jun. 17, 2014, Fair Disclosure Wire (Quarterly Earnings Reports), Accession No. 32U3101469591FDW.
Acceleron, 'Corporate Overview', considered published in Jul. 31, 2014.
Acceleron, 'Review of the Data Presented at the European Hematology Association 19th Annual Meeting', considered published on Jun. 16, 2014.
BIOSIS Accession No. 2015:276893 & Piga, A. et al., 'ACE-536 Increases Hemoglobin and Decreases Transfusion Burden and Serum Ferritin in Adults with Beta-Thalassemia: Preliminary Results from a Phase 2 Study', Blood, vol. 124, No. 21, p. 53 (Dec. 6, 2014).
Carrancio, S. et al. "An activin receptor IIA ligand trap promotes erythropoiesis resulting in a rapid induction of red blood cells and haemoglobin," British Journal of Haematology, vol. 165: 870-882 (2014).
Chantry et al., "Inhibiting Activin-A Signaling Stimulates Bone Formation and Prevents Cancer-Induced Bone Destruction in Vivo," Journal of Bone and Mineral Research, vol. 25(12): 2357-2370 (2010).
Kwiatkowski, J.L. et al., "Iron chelation therapy in sickle-cell disease and other transfusion-dependent anemias," Hematol Oncol Clin N Am., vol. 18: 1355-1377 (2004).
MacLennan et al., "Multiple Myeloma," BMJ, vol. 308:1033-1036 (1994).
Marri et al, "Human Biochemistry, Moscow," Mir, vol. 1: 34-35 (1993).
Merck Manual. Iron-Utilization Anemias (Sideroblastic Anemias), pp. 1150-1151 (1992).

The Merck Manual of Diagnosis and Therapy, 17th Edition. Nyelodysplastic Syndrome, pp. 865 and 963-955 (1999).
Nolan, V.G., et al, 'Sickle Cell Leg Ulcers: Associations with Haemolysis and SNPs in Klotho, TEK and Genes of the TGF-β/BMP Pathway:-Sickle Cell Leg Ulcers, Genetics and Haemolysis', British Journal of Haematology, 133(5), pp. 570-578 (2006).
Paulson, Robert F., "Targeting a new regulator of erythropoiesis to alleviate anemia," Nature Medicine, News and Views, vol. 20(4) (2 pages) (2014).
Suragani et al., "Transforming growth factor-β superfamily ligand trap ACE-536 corrects anemia by promoting late-stage erythropoiesis," Letters, Nature Medicine, Advance Online Publication (44 pages) (2014).
Ware, Russel, "How I use hydroxyurea to treat young patients with sickle cell anemia," Blood, vol. 115(26): 5300-5311 (2010).
Abaza, M.S.I., et al., Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin, Journal of Protein Chemistry, 11(5):433-444 (1992).
Akel, S., et al "Neutralization of Autocrine Transforming Growth Factor-β," Stem Cells, 21:557-567 (2003).
Bowie, J.U., et al., "Deciphering the Message in Protein Sequences: Tolerance to Amino Acid Substitutions," Science, 257:1306-1310 (1990).
Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-2138 (1990).
Deal, C., "Potential New Drug Targets for Osteoporosis," Nature Clinical Practice, 5(1):20-27 (2009).
Eijken, M., "The Activin A-Follistatin System: Potent Regulator of Human Extracellular Matrix Mineralization," The FASEB Journal, 21:2949-2960 (2007).
Fajardo, R. J., et al., "Treatment with a Soluble Receptor for Activin Improves Bone Mass and Structure in the Axial and Appendicular Skeleton of Female Cynomolgus Macaques (*Macaca fascicularis*)," Bone, 46:64-71 (2010).
Guo, et al., Protein Tolerance to Random Amino Acid Change. Proc. Natl. Acad. Sci. USA, 101(25):9205-9210 (Jun. 22, 2004). Epub Jun. 14, 2004.
Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).
Kuntz, "Structure-based strategies for drug design and discovery," Science, 257(5073):1078-1082 (1992).
Lotinun, S., et al., "A Soluble Activin Receptor Type IIA Fusion Protein (ACE-011) Increases Bone Mass Via a Dual Anabolic-Antiresorptive Effect in Cynomolgus Monkeys," Bone, 46:1082-1088 (2010).
Miller et al., Ligand binding to proteins: the binding landscape model. Protein Sci., 6(10):2166-79 (1997).
Mosekilde, L., et al., "Emerging Anabolic Treatments in Osteoporosis," Current Drug Safety, 6:62-74 (2011).
Perrien, D. S., et al., "Inhibin A is an Endocrine Stimulator of Bone Mass and Strength," Endocrinology, 148(4):1654-1665 (2007).
Phillips, A.J., "The challenge of gene therapy and DNA delivery," J. Pharm. Pharmacology, 53:1169-1174 (2001).
Pirollo, K.F., et al., "Targeted Delivery of Small Interfering RNA: Approaching Effective Cancer Therapies," Cancer Res., 68(5):1247-1250 (2008).
Smith, L. et al., "The analysis of doxorubicin resistance in human breast cancer cells using antibody microarrays," Mol. Cancer Therapy, vol. 5: 2115-2120 (2006).
Smith, L. et al., The Status, Quality, and Expansion of the NIH Full-Length cDNA Project: The Mammalian Gene Collection (MGC), Genome Res., vol. 14(10b): 2127-2127 (2004).
Tokuriki, N., et al., "Stability effects of mutations and protein evolvability," Current Opinion in Structural Biology, 19:596-604 (2009).

(56) References Cited

OTHER PUBLICATIONS

Trivedi, R., et al., "Investigational Anabolic Therapies for Osteoporosis," Expert Opin. Investig. Drugs, 19(8):995-1005 (2010).
Type 2 Diabetes, PubMed Health, Diseases and Conditions, U.S. National Library of Medicine, Bethesda, MD (online), Jun. 28, 2011 [retrieved on Jun. 6, 2012). Retrieved from the Internet:<URL:http://www.ncbi.nlm.nih.gov/pubmedhealth/PMH0001356/>.
Utzschneider, et al., The Role of Insulin Resistance in Nonalcoholic Fatty Liver Disease, J. Clin. Endocrinol. Metab., 91(12):4753-4761 (Dec. 2006). Epub Sep. 12, 2006.
Vidal, L., et al., "Making sense of antisense," European Journal of Cancer, 41:2812-2818 (2005).
Wang, et al., A single amino acid determines lysophospholipid specificity of the S1P1 (EDG1) and LPA1 (EDG2) phospholipid growth factor receptors. JBC 276:49213-49220 (2001).
Akpan, I., et al., "The effects of a soluble activin type IIB receptor on obesity and insulin sensitivity," International Journal of Obesity, 33(11):1265-1273 (2009).
Banks, G.B., et al., "The Value of Mammalian Models for Duchenne Muscular Dystrophy in Developing Therapeutic Strategies," Current Topics in Developmental Biology, 84:431-453 (2008).
Cirillo et al., "Hematocrit, blood pressure, and hypertension. The Gubbio Population Study," Hypertension, 20(3):319-326 (1992).
Collins, C.D., "Multidisciplinary Symposium: Haematological Malignancies," Cancer Imaging, 5:S119-S126 (2005).
Colman, P.M., et al., "Effects of amino acid sequence changes on antibody-antigen interactions," Research of Immunology, 145(1):33-36 (1994).
Deconinck, N., et al., "Pathophysiology of Duchenne Muscular Dystrophy: Current Hypotheses," Pediatr. Neurol., 36:1-7 (2007).
Gilbert, R., et al., "Prolonged dystrophin expression and functional correction of mdx mouse muscle following gene transfer with a helper-dependent (gutted) adenovirus-encoding murine dystrophin," Human Molecular Genetics, 12(11):1287-1299 (2003).
Greenspan, N.S., et al., "Defining epitopes: It's not as easy as it seems," Nature Biotechnology, 17:936-937 (1999).
Gregoriadis, G., et al., "Polysialic acids: potential in drug delivery," FEBS, 315(3):271-276 (1993).
Harrison, C.A., et al., "An Activin Mutant with Disrupted ALK4 Binding Blocks Signaling via Type II Receptors," The Journal of Biological Chemistry, 279(27):28036-28044 (2004).
Herbert, W.J., et al., The Dictionary of Immunology, Academic Press, 3rd Edition, London, 58-59 (1985).
Kaiser, J., "First Pass at Cancer Genome Reveals Complex Landscape," Science, 313:1370 (2006).
Kim, et al., "Type IIa IgG-Fc Fusion Protein, Increases Hemoglobin and Hematocrit Levels in Postmenopausal Healthy Women," Blood, 112(11):1316 (2008).
Menstruation: Absent Periods (Amenorrhea), downloaded on Jun. 14, 2010, <http://adam.about.com/reports/000101_2.htm?p=1> (11 pages).
Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.
Mickle, et al., "Genotype-Phenotype Relationships in Cystic Fibrosis," Med. Clin. North Am., 84(3):597-607 (2000).
Ngo, J.T., et al., "Computational Complexity, Protein Structure Prediction, and the Levinthal Paradox," The Protein Folding Problem and Tertiary Structure Prediction, Merz et al., eds., Birkhauser, Boston, 492-495 (1994).
Patel, K., et al., "The function of Myostatin and strategies of Myostatin blockade—new hope for therapies aimed at promoting growth of skeletal muscle," Neuromuscular Disorders, 15:117-126 (2005).
Qi, et al., "Blockade of type β transforming growth factor signaling prevents liver fibrosis and dysfunction in the rat," PNAS, 96:2345-2349 (1999).

Raju, T.S., "Glycosylation in the Fc domain of IgG increases resistance to proteolytic cleavage by papain," Biochemical and Biophysical Research Communications, 341:797-803 (2006).
Satoh, et al., "Hemodynamic changes by recombinant erythropoietin therapy in hemodialyzed patients," Hypertension, 15(3):262-266 (1990).
Vallet, S., et al., "Activin A promotes multiple myeloma-induced osteolysis and is a promising target for myeloma bone disease," PNAS, 107(11):5124-5129 (2010).
Wells, J.A., "Additivity of Mutational Effects in Proteins," Biochemistry, 29(37):8509-8517 (1990).
Zhao, B., et al., "Transgenic expression of myostatin propeptide prevents diet-induced obesity and insulin resistance," Biochemical and Biophysical Research Communications, 337:248-255 (2005).
Bogdanovich, S., et al., "Functional improvement of dystrophic muscle by myostatin blockade," Nature, 420:418-421 (2002).
Krag, T.O.B., et al., "Heregulin ameliorates the dystrophic phenotype in *mdx* mice," PNAS, 101(38):13856-13860 (2004).
Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (2009).
Miura, P., et al., "Utrophin upregulation for treating Duchenne or Becker muscular dystrophy: how close are we?," Trends in Molecular Medicine, 12(3):122-129 (2006).
Rodriquez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).
Tinsley, J., et al., "Expression of full-length utrophin prevents muscular dystrophy in *mdx* mice," Nature Medicine, 4(12):1441-1444 (1998).
Tu, P., et al., "Genetic Disruption of Myostatin Reduces the Development of Proatherogenic Dyslipidemia and Atherogenic Lesions in *Ldlr* Null Mice," Diabetes, 58:1739-1748 (2009).
Wagner, K.R., et al., "A Phase I/II trial of MYO-029 in Adult Subjects with Muscular Dystrophy," Ann. Neurol., 63:561-571 (2008).
Wagner, K.R., et al., "Loss of Myostatin Attenuates Severity of Muscular Dystrophy in *mdx* Mice," Ann. Neurol., 52:832-836 (2002).
Wagner, K.R., et al., "Muscle regeneration in the prolonged absence of myostatin," PNAS, 102(7):2519-2524 (2005).
Allendorph, G.P., et al., "Structure of the ternary signaling complex of a TGF-β superfamily member," PNAS, 103(20):7643-7648 (2006).
Greenwald, J., et al., "Three-finger toxin fold for the extracellular ligand-binding domain of the type II activin receptor serine kinase," Nature Structural Biology, 6(1):18-22 (1999).
Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.
Datta-Mannan et al, Addendum to "An Engineered Human Follistatin Variant: Insights into the Pharmacokinetic and Pharmocodynamic Relationships of a Novel Molecule with Broad Therapeutic Potential," The Journal of Pharmacology and Experimental Therapeutics, 1 page (2013).
GenBank NP_001607.1, Activin A Type II receptor precursor [*Homo sapiens*], http://www.ncbi.nlm.nih.gov/protein/4501897?sat=34&satkey=10571517 (Apr. 22, 2005); downloaded Nov. 24, 2015).
Keutmann et al, "The Role of Follistatin Domains in Follistatin Biological Action," Molecular Endocrinology, Jan; 18(1) pp. 228-240 (2003).
Pennucci et al., Multiplexed evaluation of a cell-based assay for the detection of antidrug neutralilzing antibodies to Panitumumab in human serum using automated fluorescent microsopy,: J. Biomol. Sceen. vol. 15: 644-652 (2010).
Pak et al., "Suppression of hepcidin during anemia requires erythropoietic activity," Blood, vol. 108(12): 3730-3735 (2006).

(56) References Cited

OTHER PUBLICATIONS

R&D Systems Catalogue No. AF339 Datasheet: Human Activin RIIB Antibody [retrieved on Feb. 13, 2013] Retrieved from the Internet: http://www.rndsystems.com/pdf/af339.pdf.
R&D Systems, "Antibody Reference Guide and Catalog Instructions," [retrieved on Feb. 13, 2013]; http://web.archive.org/web/20090220022132/http://rndsystems.com/DAM_public/5658.pdf; published Mar. 14, 2009 as per the Wayback Engine. See, in particular: p. 3.
Sirskyj et al., Detection of influenza A and B neutralizing antibodies in vaccinated ferrets and macaques using specific biotinstreptavidin conjugated antibodies, J. Virol. Methods. vol. 163: 459-464 (2010).
Sun Shuhan et al., "Chromosome, Gene, and Disesase," Science Press (2009).
Winkler et al., "Sclerostin Inhibition of Wnt-3a-induced C3H10T1/2 Cell Differentiation is Indirect and Mediated by Bone Morphogenetic Proteins," vol. 280(4): 2498-2502 (2005).
Acceleron Pharma Presents Positive Phase 1 Results Demonstrating ACE-011 Increases Markers of Bone Formation, Acceleron Pharma, pp. 1-2, retrieved from the Internet, www.acceleronpharma.com/contents/news/press-releases/detail.jsp/q/news-id/47> (2007).
Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).
Burdette et al., "Activin A mediates growth inhibition and cell cycle arest through Smads in human breast cancer cells." Cancer Research, 65(17):7968-7975; Abstract (2005).
Centrella et al., "Activin-A Binding and Biochemical Effects in Osteoblast-Enriched Cultures from Fetal-Rat Parietal Bone," Molecular and Cellular Biology, 11(1):250-58 (1991).
Coerver, K.A., et al., "Activin Signaling through Activin Receptor Type II Causes the Cachexia-Like Symptoms in Inhibin-Deficient Mice," Molecular Endocrinology, 10(5):534-543 (1996).
Daluiski et al., "Bone Morphogenetic Protein-3 is a Negative Regulator of Bone Density," Nature Genetics, 27:84-88 (2001).
del Re et al., "Reconstitution and Analysis of Soluble Inhibin and Activin Receptor Complexes in a Cell-free System," The Journal of Biological Chemistry, 279(51):53126-53135 (2004).
Donaldson, et al., "Activin and inhibin binding to the soluble extracellular domain of activin receptor II", Endocrinology 140(4):1760-1766(1999).
Donaldson, et al., "Molecular Cloning and Binding Properties of the Human Type II Activin Receptor", Biochemical and Biophysical Research Communications, 184(1):310-316(1992).
Fafioffe, et al.,"Activin and inhibin receptor gene expression in the ewe pituitary throughout the oestrous cycle," Journal of Endocrinology, vol. 182, pp. 55-68 (2004).
Frigon, N.L., et al, "Regulation of Globin Gene Expression in Human K562 Cells by Recombinant Activin A," Blood, 79(3):765-772 (1992).
Fuller et al., "Activin A is an Essential Cofactor for Osteoclast Induction," Biochemical and Biophysical Research Communications, 268:2-7 (2000).
Funaba et al., "Expression and Localization of Activin Receptors During Endochondral Bone Development," European Journal of Endocrinology, 144:63-71 (2001).
Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).
Gamer et al., "BMP-3 is a Novel Inhibitor of Both Activin and BMP-4 Signaling in Xenopus Embryos," Developmental Biology, 285:156-168 (2005).
Ge, G., et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).

GenBank NM_001106, Homo sapiens activin A receptor, type IIB (ACVR2B), mRNA, http://www.ncbi.nlm.nih.gov/entrez/viewer.fcgi?db=nucleotide&val=116734707 (Downloaded on Jan. 29, 2007).
Gonzalez-Cadavid, N.F., et al., "Organization of the human myostatin gene and expression in healthy men and HIV-infected men with muscle wasting," PNAS, 95:14938-14943 (1998).
Gray, et al., "Identification of a binding site on the type II activin receptor for activin and inhibin", Journal of Biological Chemistry, 275(5):3206-3212(2000).
Greenwald, et al., "The BMP7/ActRII Extracellular Domain Complex Provides New Insights into the Cooperative Nature of Receptor Assembly," Molecular Cell, vol. 11, 605-617 (2003).
Hamrick et al., "Bone Mineral Content and Density in the Humerus of Adult Myostatin-Deficient Mice," Calcified Tissue International, 71:63-68 (2002).
Hamrick, "Increased Bone Mineral Density in the Femora of GDF8 Knockout Mice," The Anatomical Record, Part A 272A:388-391 (2003).
Hamrick, M.W., et al., "Femoral Morphology and Cross-sectional Geometry of Adult Myostatin-deficient Mice," Bone, 27(3):343-349 (2000).
Harrison, et al., "Antagonists of activin signaling: mechanisms and potential biological applications," Trends in Endocrinology and Metabolism, 16(2):73-78 (2005).
Hashimoto et al., "Functional Regulation of Osteoblastic Cells by the Interaction of Activin-A with Follistatin," The Journal of Biological Chemistry, 267(7):4999-5004 (1992).
Hemmati-Brivanlou, A., et al., "A truncated activin receptor inhibits mesoderm induction and formation of axial structures in Xenopus embryos," Nature, 359:609-614 (1992).
Hilden, K., et al., "Expression of Type II Activin Receptor Genes During Differentiation of Human K562 Cells and cDNA Cloning of the Human Type IIB Activin Receptor," Blood, 83(8):2163-2170 (1994).
Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Ikenoue et al., "Inhibitory Effects of Activin-A on Osteoblast Differentiation During Cultures of Fetal Rat Calvarial Cells," Journal of Cellular Biochemistry, 75:206-214 (1999).
Kaspar, B.K., et al., "Retrograde Viral Delivery of IGF-1 Prolongs Survival in a Mouse ALS Model," Science, 301:839-842 (2003).
Knight, "Roles of Inhibins, Activins, and Follistatin in the Female Reproductive System," Frontiers in Neuroendocrinology, 17:476-509 (1996).
Kosaki, R., et al., "Left-Right Axis Malformations Associated With Mutations in ACVR2B, the Gene for Human Activin Receptor Type IIB," American Journal of Medical Genetics, 82:70-76 (1999).
Koseki, et al., "Role of TCF-b Family in Osteoclastogenesis Induced by RANKL," Cellular Signaling, 14:31-36 (2002).
Krystal et al., "Transforming Growth Factor β1 is an Inducer of Erythroid Differentiation," J. Exp. Med., 180:851-860 (1994).
Kubanek, B., "Introduction: The Role of the Microenvironment and Cytokines on the Modulation of Erythropoiesis," Annals New York Academy of Sciences, pp. 257-258 (1994).
Lazar, E., et al., "Transforming Growth Factor α: Mutation of Aspartic Acid 47 and Leucine 48 Results in Different Biological Activities," Molecular and Cellular Biology, 8(3):1247-1252 (1988).
Lebrun, J.J., et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23(2):117-122 (2006).

(56) References Cited

OTHER PUBLICATIONS

Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Maguer-Satta, V., et al, "Regulation of human erythropoiesis by activin A, BMP2, and BMP4, members of the TGFβ family," Experimental Cell Research, 282:110-120 (2003).
Matzuk et al., "Different phenotypes for mice deficient in either activins or activin receptor type II," Nature, 374:356-360 (1995).
McNally, E.M., "Powerful Genes—Myostatin Regulation of Human Muscle Mass," N. Engl. J. Med., 350(26):2642-2644 (2004).
McPherron, A.C., et al., "Regulation of Skeletal Muscle Mass in Mice by a Bew TGF-b Superfamily Member," Nature, 387:83-90 (1997).
Meriggiola et al., "Follistatin Decreases Activin-Stimulated FSH Secretion with No Effect on GnRH-Stimulated FSH Secretion in Prepubertal Male Monkeys," Endocrinology, 134(4):1967-1970 (1994).
Murase et al., "Possible Involvement of Protein Kinases and Smad2 Signaling Pathways on Osteoclast Differentiation Enhanced by Activin A," Journal of Cellular Physiology, 188:236-242 (2001).
Nagamine et al., "Immunohistochemical Detection of Activin A, Follistatin, and Activin Receptors during Fracture Healing in the Rat," Journal of Orthopaedic Research, 16:314-321 (1998).
Nakamura, K., et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).
Ogawa et al., "Bovine Bone Activin Enhances Bone Morphogenetic Protein-Induced Ectopic Bone Formation," The Journal of Biological Chemistry, 267(20):14233-14237 (1992).
Oh, S.P., et al., "Activin type IIA and IIB receptors mediate Gdf11 signaling in axial vertebral patterning," Genes & Development, 16:2749-2754 (2002).
Oue et al., "Effect of Local Injection of Activin A on Bone Formation in Newborn Rats," Bone, 15(3):361-366 (1994).
Pearsall, et al., "A Soluble Activin Receptor Type IIA (ACTRIIA) Acts as a Novel Bone Anabolic Agent," The Official Journal of the European Calcified Tissue Society, 34th Europena Symposium on Calcified Tissues, May 2007.
Pearsall, et al., "Treatment with a Soluble Activin Type II Receptor Reverses Bone Loss in Ovariectomized Mice," Journal of Bone and Mineral Research 2006 Abstracts, 21(1):s1-s530 (2006).
Rebbapragada, et al., "Myostatin Signals Through a Transforming Growth Fact b-Like Signaling Pathway to Block Adipogenesis," Molecular and Cellular Biology, 23(20):7230-7242 (2003).
"Recombinant Human Activin RIIA/Fc Chimera", R&D Systems 340-R2 (2003).
"Recombinant Human Activin RIIB/Fc Chimera", R&D Systems 339-RB/CF (2003).
Ruzek et al., "Minimal Effects on Immune Parameters Following Chronic Anti-TGF-β Monoclonal Antibody Administration to Normal Mice," Immunopharmacology and Immunotoxicology 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone, 27(1):91-96 (2000).
Sakai et al., "Activin release from bone coupled to bone resorption in organ culture of neonatal mouse calvaria," Bone, 26(3):235-240 (2000).
Sakai et al., "Involvement of Activin in the Regulation of Bone Metabolism," Molecular and Cellular Endocrinology, 180:183-188 (2001).

Sakai et al., "Local Administration of Activin Promotes Fracture Healing in the Rat Fibula Fracture Model," Bone, 25(2):191-196 (1999).
Sakai et al., "The Measurement of Activin/EDF in Mouse Serum: Evidence for Extragonadal Production," Biochemical and Biophysical Research Communications, 188(2):921-926 (1992).
Sakai, et al., "Osteogenic Activity of Activin in Young Normal Rats and Young Adult and Aged Rats after Ovarlectomy," Bone, 23:(Suppl.) 467 (1998).
Schuelke, M., et al., "Myostatin Mutation Associated with Gross Muscle Hypertrophy in a Child," New England Journal of Medicine, 350(26):2682-2688 (2004).
Shao, L., et al., "Effect of Activin A on Globin Gene Expression in Purified Human Erythroid Progenitors," Blood, 79(3):773-781 (1992).
Shav-Tal, Y., et al., "The Role of Activin A in Regulation of Hemopoiesis," Stem Cells, 20:493-500 (2002).
Shiozaki, M., et al, "Activin A: A Commitment Factor in Erythroid Differentiation," Biochemical and Biophysical Research Communications, 242:631-635 (1998).
Shiozaki, M., et al, "Evidence for the participation of endogenous activin A/erythroid differentiation factor in the regulation of erythropoiesis," Proc. Natl. Acad. Sci. USA, 89:1553-1556 (1992).
Shiozaki, M., et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shuto et al., "Osteoblasts Express Types I and II Activin Receptors During Early Intramembranous and Endochondral Bone Formation," Journal of Bone Mineral Research, 12(3):403-411 (1997).
Song, J., et al., "The Type II Activin Receptors are Essential for Egg Cylinder Growth, Gastrulation, and Rostral Head Development in Mice," Development Biology, 213:157-169 (1999).
Springer, et al., "Seventh European Congress on Clinical and Economic Aspects of Osteoporosis and Osteoarthritis," Osteoporosis International, 18(1):S29-S75 (2007).
Sun, et al., "FSH Directly Regulates Bone Mass," Cell, 125:247-260 (2006).
Thompson, et al., "Structures of an ActRIIB: activin A complex reveal a novel binding mode for TGF-beta ligand: receptor interactions", EMBO 22(7):1555-1566(2003).
Tsuchida, et al., "Activin isoforms signal through type I receptor serine/threonine kinase ALK7," Molecular and Cellular Endocrinology, vol. 220, pp. 59-65 (2004).
Weber, et al., "A slient H-bond can by mutationally activated for high-affinity interaction of BMP-2 and activin type IIB receptor, BMC Structural Biology, 7:6, 1-20 (2007).
Welt, C.K., et al., "Activin: an endocrine or panacrine agent?," European Journal of Endocrinology, 139:469-471 (1998).
Wiater, et al., "Inhibin is an Antagonist of Bone Morphogenetic Protein Signaling," The Journal of Biological Chemistry, 278(10):7934-7941 (2003).
Wolfman, N.M., et al., "Activation of latent myostatin by the BMP-1/tolloid family of metalloproteinases," PNAS, 100(26):15842-15846 (2003).
Yokota, T., et al., "Isolation and characterization of a mouse cDNA clone that expresses mast-cell growth-factor activity in monkey cells," Proc. Natl. Acad. Sci. USA, 81:1070-1074 (1984).
Yu, J., et al., "Importance of FSH-releasing protein and inhibin in erythrodifferentiation," Nature, 330:765-767 (1987).
Yu et al., "Specific roles of activin/inhibin in human erythropoiesis in vitro." Annals New York Academy of Sciences, 20(10):1243-1246 (1991).
Abbiotec: ACTR-IIA Antibody: Catalog No. 251303 (http://www.abbiotec.com) Jun. 3, 2010.
Acta Cryst.,"The CCP4 suite: programs for protein crystallography: Collaborative Computational Project, No. 4," D50: 760-763 (1994).
Anonymous "Learning about Thalassemia" <http://www.genome.gov/10001221> Accessed on Internet Jul. 9, 2013. Published Jun. 28, 2010.
Anonymous "Iron and Thalassemia," Accessed on the Internet Apr. 3, 2014 at <sickle.bwh.harvard.edu/thaliron.html>. Published Aug. 25, 1997.

(56) References Cited

OTHER PUBLICATIONS

Anti-ActRIIA Antibodies: Commercial Monoclonal Antibodies Against Human ActRIIA (2010).
"Anti-human Activin RIIA Antibody," R&D Systems, Catalog No. AF340 (Feb. 14, 2006).
Antibodies for ACVR2A: http://www.genecards.org/cgi-bin/card-disp.pl?gene=Acvr2a (Jun. 8, 2010).
Attie et al., "A Single Ascending-Dose Study of Muscle Regulator Ace-031 in Healthy volunteers," Muscle & Nerve, pp. 1-8 (2012).
Bhatia et al., Protein Glycosylation: Implications for In Vivo Functions and Therapeutic Applications. Advances in Biochemical Engineering/Biotechnology, vol. 64: 155-201 (1998).
Bork, "Powers and Pitfalls in Sequence Analysis: The 70% Hurdle," Genome Research, 10:398-400 (2000).
Cannon and Nedergaard, "Neither fat nor flesh," Nature, vol. 454(7207): 947-948 (2008).
Casset et al., "A Peptide mimetic of an anti-CD4 monoclonal antibody by rational design," Biochemical and Biophysical Research Communications, vol. 307:198-205 (2003).
CDR Definitions from Handbook of Therapeutic Antibodies, (2010).
Chang, Sam S., "Exploring the Effects of Luteinizing Hormone-Releasing Hormone Agonist Therapy on Bone Health: Implications in the Management of Prostate Cancer," Urology, vol. 52: 29-35 (2003).
Chardès et al., "Efficient amplification and direct sequencing of mouse variable regions from any immunoglobulin gene family," FEBS Lett. vol. 452(3): 386-394 (1999).
Chavez-Tapia, Norberto-C et al., "Insulin sensitizers in treatment of nonalcoholic fatty liver disease: Systematic review," World Journal of Gastroenterology, vol. 12(48): 7826-7831 (2006).
Chen et al., "Selection and Analysis of an Optimized Anti-VEGF Antibody: Crystal Structure of an Affinity-matured Fab in Complex with Antigen," J. Mol. Biol., vol. 293: 865-881 (1999).
Crisan et al., "A Reservoir of Brown Adipocyte Progenitors in Human Skeletal Muscle," Stem Cells, vol. 26(9): 2425-2433 (2008).
Database Geneseq [Online], "Variable heavy chain of anti-human Fas ligand antibody NOK-4," retrieved from EBI accession No. GSP:AAW00829; Database accession No. AAW00829; abstract, sequence (1997).
Database Geneseq [Online]; "Monoclonal antibody 10D4 HMGB1 Vkappa domain," retrieved from EBI accession No. GSP:ADY85028, Database accession No. GSP:ADY85028; abstract, sequence (2005).
Donald et al., "SDR: a database of predicted specificity-determining residues in proteins," Nucleic Acids Research, vol. 37: D191-D194 (2009).
Donaldson et al., GenBank: BAA06548.1: activin typeII A receptor precursor [*Homo sapiens*] (1992).
Dussiot et al., "An activin receptor IIA ligand trap corrects ineffective erythropoiesis in B-thalassemia," Nature Medicine, vol. 20: 398-407 (2014).
Ear et al., "RAP-011 Efficiently Rescues Erthropoiesis in Zebrafish Models of Diamond Blackfan Anemia," 55 ASH Annual Meeting and Exposition. Abstract #3702 (2013).
Elliot et al., "Enhancement of therapeutic protein in vivo activities through glycoengineering," Nature Biotechnology, vol. 21: 414-421 (2003).
Farmer, Stephen R., "Brown Fat and Skeletal Muscle: Unlikely Cousins?," Cell, vol. 134(5): 726-727 (2008).
Ferguson et al., "The role of effectors of the activin signalling pathway, activin receptors IIA and IIB, and Smad2, in patterning of tooth development," Development, vol. 128: 4605-4613 (2001).
Frankel et al., "Characterization of diphtheria fusion proteins targeted to the human interleukin-3 receptor," Protein Engineering, vol. 13(8): 575-581 (2000).
"Human Activin RIIA Antibody," R&D Systems, Tools for Cell Biology Research, Catalog No. MAB340 (Mar. 22, 2011).
Lazar, Mitchell A., "How Now, Brown Fat?" Science, vol. 321(5892): 1048-1049 (2008).

Lifespan Biosciences, Activin Receptor Type 2A (ACVR2A) Mouse anti-Human Monoclonal Antibody—LS-C33835—LifeSpan Biosciences, (2010).
Fan, et al., "Preclinical evaluation of Hematide, a novel erythropoiesis stimulating agent, for the treatment of anemia," Experimental Hematology 34, pp. 1303-1311 (2006).
Fournier et al., "Blockade of the activin receptor IIb activates functional brown adipogenesis and thermogenesis by inducing mitochondrial oxidative metabolism," Mol. Cell. Biol. vol. 32(14): 2871-2879 (2012).
Foucar, K., Myelodysplastic/ Myeloproliferative Neoplasms, Am J Clin Pathol, vol. 132: 281-289 (2009).
Haidar et al., "Paraspinal extramedullary hematopoiesis in patients with thalassemia intermedia," Eur Spine J., vol. 19: 871-878 (2010).
Harousseau et al., "Multiple Myeloma," American Society of Hematology, pp. 237-256 (2004).
Holm et al., "Functional mapping and single chain construction of the anti-cytokeratin 8 monoclonal antibody TS1," ScienceDirect; Molecular Immunology, vol. 44(6): 1075-1084 (2007).
"The Illustrated Guide to Bone Marrow Diagnosis Second Edition," Ed. By G. Kumar. Originally published 2003.
Ito et al., "Presence of activin signal transduction in normal ovarian cells and epithelial ovarian carcinoma," British Journal of Cancer, vol. 82(8): 1415-1420 (2000).
Kanemitsu, Fusae, "Clinical application of subforms of creatine kinase MM and macro creatine kinases," Journal of Chromatography, vol. 526: 423-438 (1990).
Koncarevic et al., "A Soluble Activin Receptor Type IIB Prevents the Effects of Angdrogen Deprivation on Body Composition and Bone Health," Endocrinology, vol. 151(9); 4289-4300 (2010).
Kos et al., "Activin type II receptors in embryonic dorsal root ganglion neurons of the chicken," J. Neurobiol., vol. 47(2): 93-108 (2001).
Liu et al., "Characterization of isoforms of activin receptor-interacting protein 2 that augment activin signaling," Journal of Endocrinology, vol. 189: 409-421 (2006).
Ma, "Animal Models of Disease," Modern Drug Discovery, 30-36 (2004).
MacCallum et al., "Antibody-antigen Interactions: Contact Analysis and Binding site Topography," J. Mol. Biol, vol. 262: 732-745 (1996).
McCarthy et al., Monoclonal antibodies that recognize the type-2 activin receptor, ACTR2, Hybridoma, vol. 13(3): 199-203 (1994) (abstract).
McPherron and Lee, "Suppression of body fat accumulation in myostatin-deficient mice," The Journal of Clinical Investigation, vol. 109(5): 595-601 (2002).
Monoclonal Anti-human Activin RII Antibody, R&D Systems, Catalog No. MAB3391 (Feb. 18, 2009).
Moore et al., "Molecular Basis of Bone Morphogenetic Protein-15 Signaling in Granulosa Cells," The Journal of Biological Chemistry, vol. 278(1): 304-310 (2003).
Morrison et al., "A soluble activin type IIB receptor improves function in a mouse model of amyotrophic lateral sclerosis," Experimental Neurology vol. 217: 258-268 (2009).
The website downloaded Oct. 28, 2014 from the Multiple Myeloma Research Foundation, themmrf.org/multiple-myeloma/symptoms/bone-lesions/, 2 pages total.
Nemeth, E., "Hepcidin in ?-thalassemia," Annals of the New York Academy of Sciences, vol. 1202: 31-35. Published Aug. 2, 2010.
NIH website downloaded May 28, 2014 from: web.archive.org/web/20030409091558/http://www.cc.nih .gov/ccc/patient_education/pepubs/subq.pdf; Patient Information Publications: Giving a Subcutaneous Injection ( 6 pages total).
Padlan et al., "Identification of specificity-determining residues in antibodies," The FASEB Journal, vol. 9: 133-139 (1995).
Pakula and Sauer, "Genetic analysis of protein stability and function," Annu. Rev. Genet., vol. 23: 289-310 (1989).
Paul, William E., Fundamental Immunology, 3rd edition, Raven Press, New York, 1003: 292-295 (1999).
Pearsall et al., An investigative pharmacology study of a GDF-8 (myostatin) inhibitor, ACE-031, in the common Marmoset (*Callithrix jacchus*), Database Biosis, Biosciences Information Service,

(56) References Cited

OTHER PUBLICATIONS

Accession No. PREV201200750016; Faseb Journal, vol. 22, Experimental Biology Annual Meeting, San Diego, CA Apr. 5-9, 2008 (Abstract).
Pearsall, R.S., et al., "A soluble activin Type IIA receptor induces bone formation and improves skeletal integrity", PNAS, 105(19):7082-7087 (2008).
Seale et al., "PRDM16 controls a brown fat/skeletal muscle switch," Nature, vol. 454(7207): 961-967 (2008).
Shao, L., et al., "Efficient synthesis of globoside and isoglobosidetetrasaccharides by using beta (1-->3) N-acetylgalactosaminyltransferase/UDP-N-acetyglucosamine C4 epimerase fusion protein," Chem Commun.: 1422-1423 (2003).
Shapiro et al., "Side Effects of Adjuvant Treatment of Breast Cancer," New England Journal of Medicine, vol. 344: 1997-2008 (2001).
Shi et al., "Energy Balance, Myostatin, and GILZ: Factors Regulating Adipocyte Differentiation in Belly and Bone," PPAR Research, pp. 1-12 (2007).
Shoji et al., "Identification and Characterization of a PDZ Protein That Interacts with Activin Type II Receptors," The Journal of Biological Chemistry, vol. 275(8): 5485-5492 (2000).
Suragani et al., "4236 ACE-536, a Modified Type II Activin Receptor Increases Red Blood Cells in Vivo by Promoting Maturation of Late Stage Erythroblasts," 52nd ASH Annual Meeting and Expositions, Orange County Convention Center, Orlando, FL Dec. 4-7, 2010. (abstract).
Swanson et al., "Use of Biosensors to Monitor the Immune Response," Biologics, vol. 109: 71-78 (2000).
Swanson, S. J., "New Technologies for the Detection of Antibodies to Therapeutic Proteins," Immunogenicity of Therapeutics Biological Products, vol. 112: 127-133 (2003).
Tanno, T. and Miller, J.L., "Iron Loading and Overloading due to Ineffective Erythropoiesis," Advances in Hematology, Article ID 358283, Chapter 2 (Abstract) (2010). (orig ISR 060-WO1).
Thorpe and Swanson, "Current methods for Detecting Antibodies against Erythropoietin and Other Recombinant Proteins," Clinical and Diagnostic Laboratory Immunology, vol. 12(1): 28-39 (2005).
Truksa et al., "Bone morphogenetic proteins 2, 4, and 9 stimulate murine hepcidin 1 expression independently of Hfe, transferrin receptor 2 (Tfr2), and IL-6," PNAS, vol. 103(27): 10289-10293 (2006).
Tseng, Yu-Hua et al., "New role of bone morphogenetic protein 7 in brown adipogenesis and energy expenditure," Nature: International Weekly Journal of Science (and Supplementary Information), vol. 454(7207): 1000-1004 (2008).

US Biological Technical Data Sheet for A0856-10A, accessed on Feb. 20, 2013.
US Biological, Activin Receptor Type IIA (RIIA) A0856-05E www.usbio.net/technicalsheet.php?item=A0856-05E dated Jun. 8, 2010.
Ward, R., "An update on disordered iron metabolism and iron overload," Hematology, vol. 15(5): 311-317 (2010).
Wong et al., "Validation parameters for a novel biosensor assay which simultaneously measures serum concentrations of a humanized monoclonal antibody and detects induced antibodies," Journal of Immunological Methods, vol. 209: 1-15 (1997).
Yamato et al., "Induction of apoptosis in Myeloma Cells with Activin A," Japanese Journal of Clinical Hematology; 37th Annual Meeting, Symposium 3, Apoptosis in Blood Disorders, 37:7, pp. 564-567) (2012). (translated and original).
Vajdos et al., "Comprehensive Functional Maps of the Antigen-binding Site of an Anti-ErbB2 Antibody Obtained with Shotgun Scanning mutagenesis," J. Mol. Biol., vol. 320(2): 415-428 (2002).
Zatz et al., "Serum creatine-kinase (CK) and pyruvate-kinase (PK) activities in Duchenne (DMD) as compared with Becker (BMD) muscular dystrophy," Journal of the Neurological Sciences, vol. 102: 190-196 (1991).
Zhang et al., Effects of Activin A on the Activities of the Mouse Peritoneal Macrophages, Cellular & Molecular Immunology, vol. 2(1): 63-67 (2005).
Chen, et al. "Regulation of Cell Proliferation, Apoptosis, and Carcinogenesis by Activin," The Society for Experimental Biology and Medicine, 227(2):75-87 (2002).
Gupta, V. et al., "Transforming growth factor-β superfamily: Evaluatrion as breast cancer biomarkers and preventive agents", Current Cancer Drug Targets, 4:165-182 (2004).
Krneta, et al., "Dissociation of Angiogenesis and Tumorigenesis in Follistatin- and Activin-Expressing Tumors," Cancer Research, 66(11):5686-5695 (2006).
McPherson, S.J. et al., "Growth inhibitory response to activin A and B by human prostate tumour cell lines LNCaP and DU1465", Journal of Endocrinology, Bristol, GB, 154:535-545 (1997).
Pearsall, R.S. et al., "A solulble activin Type IIA receptor induces bone formatrion and improves skeletal integrity", PNAS, 105(9):7082-7087 (2008).
Reis, et al., "Activin, Inhibin and the Human Breast," Molecular and Cellular Edocrinology 225:77-82 (2004).
Risbridger, et al., "Activins and Inhibins in Endocrine and Other Tumors," Endocrine Reviews 22(6):836-858 (2001).
Robinson, et al., "Inhibins and Activins Regulate Mammary Epithelial Cell Differentiation Through Mesenchymal-epithelial Interactions," Development 124:2701-2708 (1997).

\* cited by examiner

ACTIVIN-ACTRIIA ANTAGONISTS AND USES FOR TREATING OR PREVENTING BREAST CANCER

CROSS-REFERENCE TO RELATED APPLICATIONS

This application claims the benefit of U.S. Provisional Application Ser. No. 60/899,070, filed Feb. 1, 2007 and U.S. Provisional Application Ser. No. 61/000,540 filed Oct. 25, 2007. All the teachings of the above-referenced applications are incorporated herein by reference.

SEQUENCE LISTING

The instant application contains a Sequence Listing which has been submitted via EFS-Web and is hereby incorporated by reference in its entirety. Said ASCII copy, created on Mar. 4, 2010, is named PHPH018SS.txt, and is 24,551 bytes in size.

BACKGROUND OF THE INVENTION

Breast cancer is the most common type of cancer among women in Western nations, affecting more than 180,000 women in the U.S. each year. The disease arises in the mammary gland, which is made up of a branching duct system. Each mammary gland, or breast, contains 15 to 20 sections called lobes, and each lobe contains a series of branched ducts that drain into the nipple. Epithelial cells that line each duct are responsible for milk production. Invasive breast cancer is thought to originate from normal epithelium of the terminal duct/lobular unit through a series of increasingly abnormal proliferative lesions. Once the tumor acquires the ability to metastasize, breast cancer cells spread to other organs, making treatment increasingly more difficult. The most common sites of breast cancer metastases are the lung, liver, and bones. Metastases to the bone are commonly associated with severe pain, loss of bone, and increased risk of fractures. Many anti-estrogenic therapies used in the treatment of breast cancer are also associated with accelerated bone loss.

Patients diagnosed with breast cancer typically undergo surgery and/or radiotherapy to treat the primary tumor, followed by adjuvant therapy to treat any cancer cells that may have spread to distant sites. Adjuvant therapy consists of cytotoxic chemotherapy and/or endocrine therapy. Although chemotherapy has been effective in treating various types of malignancies, many anti-neoplastic compounds induce undesirable side effects. Additionally, many tumors either fail to respond or become resistant to chemotherapy and endocrine therapies. While adjuvant therapy has improved the mortality rate among breast cancer patients, the 10-year survival rate for patients with the most common histopathological types of invasive breast cancer is still only 35-50% (Weigelt et al. 2005 Nat. Rev. Cancer 5: 591-602). Further, due to poor prognosis criteria, many women that would be cured by local treatment alone receive adjuvant therapy unnecessarily.

Consequently, more efficient and effective molecular targets against breast cancer are needed. Alternative therapies that are less toxic and/or more effective than chemotherapy and endocrine therapies would improve treatment regimens and increase survival. Further, agents that can be used as preventative treatments for patients that may be at risk for developing invasive or metastatic breast cancer would be useful in the clinic. It is an object of the present disclosure, therefore, to provide alternative compositions and methods for treating breast cancer or inhibiting or preventing the progression of breast cancer in patients.

SUMMARY OF THE INVENTION

In part, the disclosure relates to the use of activin antagonists, as well as ActRIIa antagonists, to treat or prevent breast cancer or bone loss associated with breast cancer. In particular, the disclosure provides methods for treating or preventing breast cancer using a soluble form of ActRIIa that acts as an inhibitor of activin. While soluble ActRIIa may affect cancer cell growth or survival through a mechanism other than activin antagonism, desirable therapeutic agents may nonetheless be selected on the basis of activin antagonism or ActRIIa antagonism or both. Such agents are referred to collectively as activin-ActRIIa antagonists. Therefore, in certain embodiments, the disclosure provides methods for using activin-ActRIIa antagonists, including, for example, activin-binding ActRIIa polypeptides, anti-activin antibodies, anti-ActRIIa antibodies, activin- or ActRIIa-targeted small molecules and aptamers, and nucleic acids that decrease expression of activin and ActRIIa, to treat or prevent breast cancer in patients in need thereof. As described in U.S. patent application Ser. No. 11/603,485, incorporated by reference herein, activin-ActRIIa antagonists can be used to promote bone growth and increase bone density. As described herein, such antagonists can also be used to treat or prevent breast cancer, breast cancer metastases to the bone and bone loss associated with breast cancer.

In certain aspects, the disclosure provides methods for treating or preventing breast cancer using polypeptides comprising a soluble, activin-binding ActRIIa polypeptide that binds to activin. ActRIIa polypeptides may be formulated as a pharmaceutical preparation comprising the activin-binding ActRIIa polypeptide and a pharmaceutically acceptable carrier. The activin-binding ActRIIa polypeptide may bind to activin with a $K_D$ less than 1 micromolar or less than 100, 10 or 1 nanomolar. Optionally, the activin-binding ActRIIa polypeptide selectively binds activin versus GDF11 and/or GDF8, and optionally with a $K_D$ that is at least 10-fold, 20-fold or 50-fold lower with respect to activin than with respect to GDF11 and/or GDF8. While not wishing to be bound to a particular mechanism of action, it is expected that this degree of selectivity for activin inhibition over GDF11/GDF8 inhibition accounts for effects on bone or tumor survival or growth without a consistently measurable effect on muscle. In many embodiments, an ActRIIa polypeptide will be selected for causing less than 15%, less than 10% or less than 5% increase in muscle at doses that achieve desirable effects on cancer cells. The composition may be at least 95% pure, with respect to other polypeptide components, as assessed by size exclusion chromatography, and optionally, the composition is at least 98% pure. An activin-binding ActRIIa polypeptide for use in such a preparation may be any of those disclosed herein, such as a polypeptide having an amino acid sequence selected from SEQ ID NOs: 2, 3, 7 or 12, or having an amino acid sequence that is at least 80%, 85%, 90%, 95%, 97% or 99% identical to an amino acid sequence selected from SEQ ID NOs: 2, 3, 7, 12 or 13. An activin-binding ActRIIa polypeptide may include a functional fragment of a natural ActRIIa polypeptide, such as one comprising at least 10, 20, 30, 50 or 90 or more amino acids of a sequence selected from SEQ ID NOs: 1-3 or a sequence of SEQ ID NO: 2, lacking the C-terminal 10 to 15 amino acids (the "tail").

A soluble, activin-binding ActRIIa polypeptide may include one or more alterations in the amino acid sequence (e.g., in the ligand-binding domain) relative to a naturally occurring ActRIIa polypeptide. Examples of altered ActRIIa polypeptides are provided in WO 2006/012627, pp. 59-60, incorporated by reference herein. The alteration in the amino acid sequence may, for example, alter glycosylation of the polypeptide when produced in a mammalian, insect or other eukaryotic cell or alter proteolytic cleavage of the polypeptide relative to the naturally occurring ActRIIa polypeptide.

An activin-binding ActRIIa polypeptide may be a fusion protein that has, as one domain, an ActRIIa polypeptide (e.g., a ligand-binding portion of an ActRIIa) and one or more additional domains that provide a desirable property, such as improved pharmacokinetics, easier purification, enhanced targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. An activin-binding ActRIIa fusion protein may include an immunoglobulin Fc domain (wild-type or mutant) or a serum albumin or other polypeptide portion that provides desirable properties such as improved pharmacokinetics, improved solubility or improved stability. In a preferred embodiment, an ActRIIa-Fc fusion comprises a relatively unstructured linker positioned between the Fc domain and the extracellular ActRIIa domain. This unstructured linker may correspond to the roughly 15 amino acid unstructured region at the C-terminal end of the extracellular domain of ActRIIa (the "tail"), or it may be an artificial sequence of 1, 2, 3, 4 or 5 amino acids or a length of between 5 and 15, 20, 30, 50 or more amino acids that are relatively free of secondary structure, or a mixture of both. A linker may be rich in glycine and proline residues and may, for example, contain a single sequence of threonine/serine and glycines or repeating sequences of threonine/serine and glycines (e.g., $TG_4$ (SEQ ID NO: 15) or $SG_4$ (SEQ ID NO: 16) singlets or repeats). A fusion protein may include a purification subsequence, such as an epitope tag, a FLAG tag, a polyhistidine sequence, and a GST fusion. Optionally, a soluble ActRIIa polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as a compound that is used to treat a bone disorder. Preferably, a pharmaceutical preparation is substantially pyrogen free. In general, it is preferable that an ActRIIa protein be expressed in a mammalian cell line that mediates suitably natural glycosylation of the ActRIIa protein so as to diminish the likelihood of an unfavorable immune response in a patient. Human and CHO cell lines have been used successfully, and it is expected that other common mammalian expression systems will be useful. Additionally, yeast and other cell types have been genetically altered to express mammalian enzymes that catalyze glycosylation, thus allowing the generation of tightly controlled mammalian-like glycosylation on proteins expressed in these non-mammalian cells. These recombinant cell lines may also be used to express the proteins described herein.

As described herein, ActRIIa proteins designated ActRIIa-Fc (a form with a minimal linker between the ActRIIa portion and the Fc portion) have desirable properties, including selective binding to activin versus GDF8 and/or GDF11, high affinity ligand binding and serum half life greater than two weeks in animal models. In certain embodiments the invention provides methods for treating or preventing breast cancer using ActRIIa-Fc polypeptides and pharmaceutical preparations comprising such polypeptides and a pharmaceutically acceptable excipient.

In certain aspects, the disclosure provides methods for treating or preventing breast cancer using nucleic acids encoding a soluble activin-binding ActRIIa polypeptide. An isolated polynucleotide may comprise a coding sequence for a soluble, activin-binding ActRIIa polypeptide, such as described above. For example, an isolated nucleic acid may include a sequence coding for an extracellular domain (e.g., ligand-binding domain) of an ActRIIa and a sequence that would code for part or all of the transmembrane domain and/or the cytoplasmic domain of an ActRIIa, but for a stop codon positioned within the transmembrane domain or the cytoplasmic domain, or positioned between the extracellular domain and the transmembrane domain or cytoplasmic domain. For example, an isolated polynucleotide may comprise a full-length ActRIIa polynucleotide sequence such as SEQ ID NO: 4 or 5, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ActRIIa. A preferred nucleic acid sequence is SEQ ID NO: 14. Nucleic acids useful in accordance with the methods described herein may be operably linked to a promoter for expression, and the disclosure provides cells transformed with such recombinant polynucleotides. Preferably the cell is a mammalian cell such as a Chinese hamster ovary (CHO) cell.

The disclosure also provides methods for making a soluble, activin-binding ActRIIa polypeptide that can be used for treating or preventing breast cancer. Such a method may include expressing any of the nucleic acids (e.g., SEQ ID NO: 4, 5 or 14) disclosed herein in a suitable cell, such as a CHO cell. Such a method may comprise: a) culturing a cell under conditions suitable for expression of the soluble ActRIIa polypeptide, wherein said cell is transformed with a soluble ActRIIa expression construct; and b) recovering the soluble ActRIIa polypeptide so expressed. Soluble ActRIIa polypeptides may be recovered as crude, partially purified or highly purified fractions. Purification may be achieved by a series of purification steps, including, for example, one, two or three or more of the following, in any order: protein A chromatography, anion exchange chromatography (e.g., Q sepharose), hydrophobic interaction chromatography (e.g., phenylsepharose), size exclusion chromatography, and cation exchange chromatography.

In certain aspects, an activin-ActRIIa antagonist disclosed herein, such as a soluble, activin-binding ActRIIa polypeptide, may be used in a method for treating, preventing or inhibiting breast cancer in a subject, including, for example, methods for delaying the onset of breast cancer, inhibiting the progression of breast cancer, reducing tumor size, preventing tumor growth, delaying the onset of metastasis or preventing metastasis, including metastasis to bone. In certain embodiments, the disclosure provides methods for decreasing or inhibiting the growth or survival of breast cancer cells in patients in need thereof. A method may comprise administering to a subject in need thereof an effective amount of activin-ActRIIa antagonist. In certain aspects, the disclosure provides uses of activin-ActRIIa antagonists for making a medicament for the treatment or prevention of breast cancer as described herein. The disclosure also relates to combination therapies comprising an activin-ActRIIa antagonist and radiation therapy, chemotherapy (e.g., a cytotoxic agent), and/or endocrine therapy. The antagonist may be an ActRIIa-Fc fusion protein, wherein the ActRIIa-Fc fusion protein comprises an amino acid sequence that is at least 90% identical to the amino acid sequence of SEQ ID NO:3.

In further embodiments, the present invention relates to methods of preventing or delaying the onset of breast cancer in patients with one or more breast cancer risk factors. In some embodiments, the invention relates to methods of preventing or delaying the onset of metastatic disease in patients already diagnosed with a primary breast tumor or with a proliferative lesion of the breast. The method of preventing or delaying the onset of breast cancer in a human patient may comprise administering to a human patient in need thereof an effective amount of a polypeptide selected from the group consisting of: a) a polypeptide comprising an amino acid sequence at least 90% identical to SEQ ID NO:2; b) a polypeptide comprising an amino acid sequence at least 90% identical to SEQ ID NO:3; and c) a polypeptide comprising at least 50 consecutive amino acids selected from SEQ ID NO: 2.

Other embodiments of the invention relate to a method of inhibiting activin-mediated signaling in a human patient with breast cancer. In certain embodiments, the method comprises administering to the human patient an effective amount of an activin-ActRIIa antagonist. In further embodiments, the antagonist is a polypeptide selected from the group consisting of: a) a polypeptide comprising an amino acid sequence at least 90% identical to SEQ ID NO:2; b) a polypeptide comprising an amino acid sequence at least 90% identical to SEQ ID NO:3; and c) a polypeptide comprising at least 50 consecutive amino acids selected from SEQ ID NO: 2.

In certain aspects, the disclosure provides a method for identifying an agent that inhibits the growth or survival of cancer cells (e.g., breast cancer cells). The method comprises: a) identifying a test agent that binds to activin or a ligand-binding domain of an ActRIIa polypeptide; and b) evaluating the effect of the agent on the proliferation, survival, or apoptosis of cancer cells.

DETAILED DESCRIPTION OF THE INVENTION

1. Overview

Figure 1:
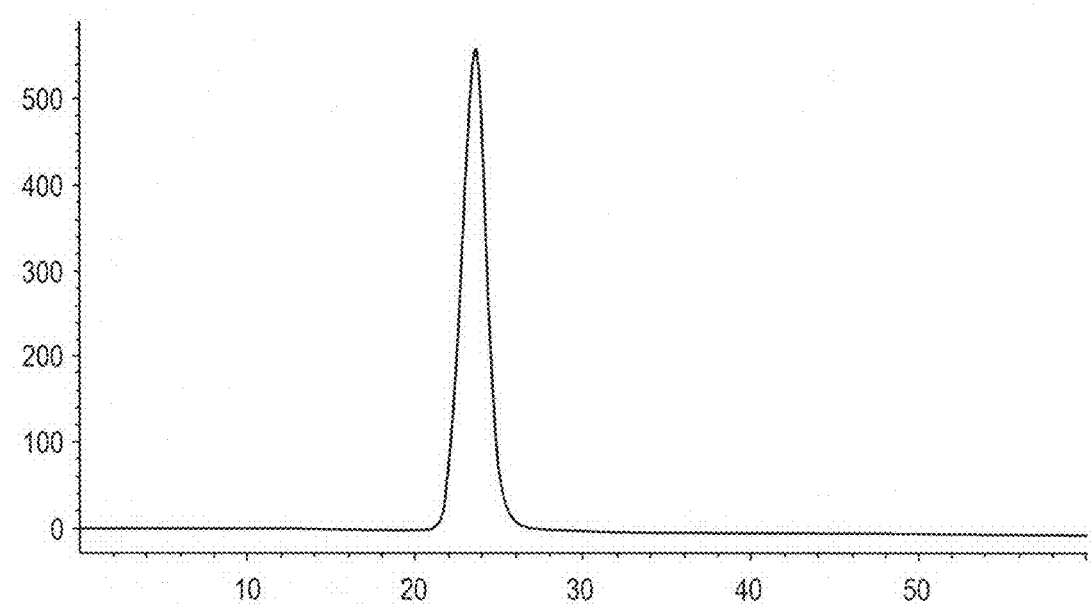
FIG. 1 shows the purification of ActRIIa-hFc expressed in CHO cells. The protein purifies as a single, well-defined peak as visualized by sizing column (left panel) and Coomassie stained SDS-PAGE (right panel) (left lane: molecular weight standards; right lane: ActRIIa-hFc).
Figure 1:
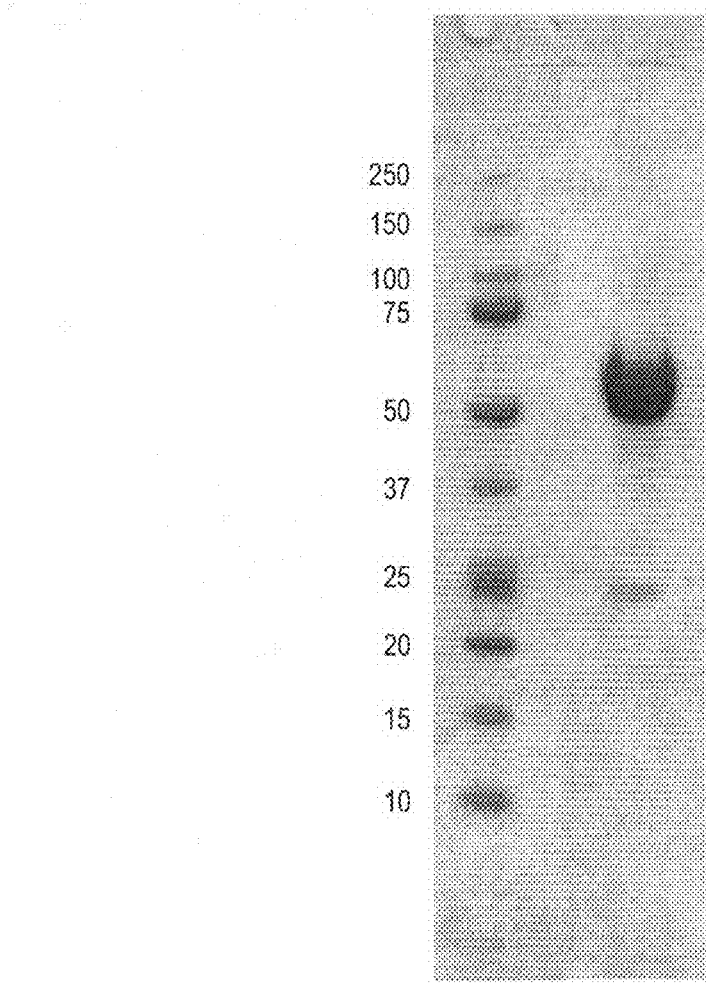

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin branches, whose members have diverse, often complementary effects. By manipulating the activity of a member of the TGF-beta family, it is often possible to cause significant physiological changes, in an organism. For example, the Piedmontese and Belgian Blue cattle breeds carry a loss-of-function mutation in the GDF8 (also called myostatin) gene that causes a marked increase in muscle mass. Grobet et al., Nat. Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Activins are dimeric polypeptide growth factors that belong to the TGF-beta superfamily. There are three principal activin forms (A, B, and AB) that are homo/heterodimers of two closely related $\beta$ subunits ($\beta_A\beta_A$, $\beta_B\beta_B$, and $\beta_A\beta_B$, respectively). The human genome also encodes an activin C and an activin E, which are primarily expressed in the liver, and heterodimeric forms containing $\beta_C$ or $\beta_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc Soc Ep Biol Med. 198:500-512; Dyson et al., 1997, Curr Biol. 7:81-84; Woodruff, 1998, Biochem Pharmacol. 55:953-963). In addition, it has been shown that activin B is involved in the regulation of mammary epithelial cell differentiation in mice (Robinson and Hennighausen, 1997 Development 124: 2701-2708). In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP) and $\alpha_2$-macroglobulin.

TGF-$\beta$ signals are mediated by heteromeric complexes of type I and type II serine/threonine kinase receptors, which phosphorylate and activate downstream Smad proteins upon ligand stimulation (Massagué, 2000, Nat. Rev. Mol. Cell. Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors, ActRIIa and ActRIIb, have been identified as the type II receptors for activins (Mathews and Vale, 1991, Cell 65:973-982; Attisano et al., 1992, Cell 68: 97-108). Besides activins, ActRIIa and ActRIIb can biochemically interact with several other TGF-$\beta$ family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell. 7: 949-957; Oh et al., 2002, Genes Dev. 16:2749-54). ALK4 is the primary type I receptor for activins, particularly for activin A, and ALK-7 may serve as a receptor for activins as well, particularly for activin B.

As described herein, a soluble ActRIIa polypeptide (sActRIIa), which shows substantial preference in binding to activin A as opposed to other TGF-beta family members, such as GDF8 or GDF11, may be used to treat or prevent cancer, particularly breast cancer. While not wishing to be bound to any particular mechanism, it is expected that the effect of sActRIIa is caused primarily by an activin antagonist effect, given the very strong activin binding (picomolar dissociation constant) exhibited by the particular sActRIIa construct used in these studies. Activin-ActRIIa antagonists include, for example, activin-binding soluble ActRIIa polypeptides, antibodies that bind to activin (particularly the activin A or B subunits, also referred to as βA or βB) and disrupt ActRIIa binding, antibodies that bind to ActRIIa and disrupt activin binding, non-antibody proteins selected for activin or ActRIIa binding (see e.g., WO/2002/088171, WO/2006/055689, and WO/2002/032925 for examples of such proteins and methods for design and selection of same), randomized peptides selected for activin or ActRIIa binding, often affixed to an Fc domain. Two different proteins (or other moieties) with activin or ActRIIa binding activity, especially activin binders that block the type I (e.g., a soluble type I activin receptor) and type II (e.g., a soluble type II activin receptor) binding sites, respectively, may be linked together to create a bifunctional binding molecule. Nucleic acid aptamers, small molecules and other agents that inhibit the activin-ActRIIa signaling axis may also be used. Various proteins have activin-ActRIIa antagonist activity, including inhibin (i.e., inhibin alpha subunit), although inhibin does not universally antagonize activin in all tissues, follistatin (e.g., follistatin-288 and follistatin-315), FSRP, activin C, alpha(2)-macroglobulin, and an M108A (methionine to alanine change at position 108) mutant activin A. Generally, alternative forms of activin, particularly those with alterations in the type I receptor binding domain can bind to type II receptors and fail to form an active ternary complex, thus acting as antagonists. Additionally, nucleic acids, such as antisense molecules, siRNAs or ribozymes that inhibit activin A, B, C or E, or, particularly, ActRIIa expression, can be used as activin-ActRIIa antagonists. The activin-ActRIIa antagonist to be used may exhibit selectivity for inhibiting activin-mediated signaling versus other members of the TGF-beta family, and particularly with respect to GDF8 and GDF11. Soluble ActRIIb proteins do bind to activin, however, the wild type protein does not exhibit significant selectivity in binding to activin versus GDF8/11. Nonetheless, such ActRIIb polypeptides, as well as altered forms of ActRIIb with different binding properties (see, e.g., WO 2006/012627, pp. 55-59, incorporated herein by reference) may achieve the desired effects on cancer cells. Native or altered ActRIIb may be given added specificity for activin by coupling with a second, activin-selective binding agent.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

The term "breast cancer" refers to any proliferative lesion or proliferative abnormality of the breast including, for example, benign lesions, pre-malignant and malignant lesions, solid tumors, and metastatic disease (both locally metastatic, e.g., stage III, and more widely metastatic, e.g., stage 1V). Breast cancer includes but is not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer. Breast cancer also refers to disease in other organs such as lung, liver, and bone, that originated from a metastatic lesion in the breast. Breast cancer also encompasses both hormone-responsive and hormone-independent cancers. Generally, hormone-independent breast cancers are characterized by the absence or reduced levels of estrogen and/or progesterone receptors, and these cancers are typically refractory to treatment with antihormonal (especially antiestrogenic) therapies. Breast cancers are also categorized on the basis of Her2 expression, with Her2$^+$ tumors having a worse prognosis than Her2$^-$ tumors.

2. ActRIIa Polypeptides

In certain aspects, the present invention relates to methods for treating or preventing breast cancer using ActRIIa polypeptides. As used herein, the term "ActRIIa" refers to a family of activin receptor type IIa (ActRIIa) proteins from any species and variants derived from such ActRIIa proteins by mutagenesis or other modification. Reference to ActRIIa herein is understood to be a reference to any one of the currently identified forms. Members of the ActRIIa family are generally transmembrane proteins, composed of a ligand-binding extracellular domain with a cysteine-rich region, a transmembrane domain, and a cytoplasmic domain with predicted serine/threonine kinase activity.

The term "ActRIIa polypeptide" includes polypeptides comprising any naturally occurring polypeptide of an ActRIIa family member as well as any variants thereof (including mutants, fragments, fusions, and peptidomimetic forms) that retain a useful activity. See, for example, WO/2006/012627. For example, ActRIIa polypeptides include polypeptides derived from the sequence of any known ActRIIa having a sequence at least about 80% identical to the sequence of an ActRIIa polypeptide, and optionally at least 85%, 90%, 95%, 97%, 99% or greater identity. For example, an ActRIIa polypeptide of the invention may bind to and inhibit the function of an ActRIIa protein and/or activin. An ActRIIa polypeptide may be selected for activity in inhibiting cancer cell proliferation or survival in vivo. Examples of ActRIIa polypeptides include human ActRIIa precursor polypeptide (SEQ ID NO: 1) and soluble human ActRIIa polypeptides (e.g., SEQ ID NOs: 2, 3, 7 and 12).

The human ActRIIa precursor protein sequence is as follows:

(SEQ ID NO: 1)
MGAAAKLAFAVFLISCSSGAILGRSETQECLFFNANWEKDRTNQTGVEPC

YGDKDKRRHCFATWKNISGSIEIVKQGCWLDDINCYDRTDCVEKKDSPEV

YFCCCEGNMCNEKFSYFPEMEVTQPTSNPVTPKPPYYNILLYSLVPLMLI

AGIVICAFWVYRHHKMAYPPVLVPTQDPGPPPPSPLLGLKPLQLLEVKAR

GRFGCVWKAQLLNEYVAVKIFPIQDKQSWQNEYEVYSLPGMKHENILQFI

GAEKRGTSVDVDLWLITAFHEKGSLSDFLKANVVSWNELCHIAETMARGL

AYLHEDIPGLKDGHKPAISHRDIKSKNVLLKNNLTACIADFGLALKFEAG

KSAGDTHGQVGTRRYMAPEVLEGAINFQRDAFLRIDMYAMGLVLWELASR

CTAADGPVDEYMLPFEEEIGQHPSLEDMQEVVVHKKKRPVLRDYWQKHAG

MAMLCETIEECWDHDAEARLSAGCVGERITQMQRLTNIITTEDIVTVVTM

VTNVDFPPKESSL

The signal peptide is single underlined; the extracellular domain is in bold and the potential N-linked glycosylation sites are double underlined.

The human ActRIIa soluble (extracellular), processed polypeptide sequence is as follows:

(SEQ ID NO: 2)
ILGRSETQECLFFNANWEKLRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP

It should be noted that the N-terminal sequence beginning "ILG . . . " has been experimentally determined and differs from the "AIL . . . " N-terminal sequence that is commonly proposed in the literature. The C-temminal "tail" of the extracellular domain is underlined. The sequence with the "tail" deleted (a A 15 sequence) is as follows:

(SEQ ID NO: 3)
ILGRSETQECLFFNANWEKDRTNQTGVEPCYGDKDKRRHCFATWKNISG

SIEIVKQGCWLDDINCYDRTDCVEKKDSPEVYFCCCEGNMCNEKFSYFP

EM

The nucleic acid sequence encoding human ActRIIa precursor protein is as follows (nucleotides 164-1705 of Genbank entry NM001616):

(SEQ ID NO: 4)
ATGGGAGCTGCTGCAAAGTTGGCGTTTGCCGTCTTTCTTATCTCCTGTTC

TTCAGGTGCTATACTTGGTAGATCAGAAACTCAGGAGTGTCTTTTCTTTA

ATGCTAATTGGGAAAAAGACAGAACCAATCAAACTGGTGTTGAACCGTGT

TATGGTGACAAAGATAAACGGCGGCATTGTTTTGCTACCTGGAAGAATAT

TTCTGGTTCCATTGAAATAGTGAAACAAGGTTGTTGGCTGGATGATATCA

ACTGCTATGACAGGACTGATTGTGTAGAAAAAAAAGACAGCCCTGAAGTA

TATTTTTGTTGCTGTGAGGGCAATATGTGTAATGAAAAGTTTTCTTATTT

TCCAGAGATGGAAGTCACACAGCCCACTTCAAATCCAGTTACACCTAAGC

CACCCTATTACAACATCCTGCTCTATTCCTTGGTGCCACTTATGTTAATT

GCGGGGATTGTCATTTGTGCATTTTGGGTGTACAGGCATCACAAGATGGC

CTACCCTCCTGTACTTGTTCCAACTCAAGACCCAGGACCACCCCCACCTT

CTCCATTACTAGGGTTGAAACCACTGCAGTTATTAGAAGTGAAAGCAAGG

GGAAGATTTGGTTGTGTCTGGAAAGCCCAGTTGCTTAACGAATATGTGGC

TGTCAAATATTTCCAATACAGGACAAACAGTCATGGCAAAATGAATACG

AAGTCTACAGTTTGCCTGGAATGAAGCATGAGAACATATTACAGTTCATT

GGTGCAGAAAAACGAGGCACCAGTGTTGATGTGGATCTTTGGCTGATGAC

AGCATTTCATGAAAAGGGTTCACTATCAGACTTTCTTAAGGCTAATGTGG

TCTCTTGGAATGAACTGTGTCATATTGCAGAAACCATGGCTAGAGGATTG

GCATATTTACATGAGGATATACCTGGCCTAAAAGATGGCCACAAACCTGC

CATATCTCACAGGGACATCAAAAGTAAAAATGTGCTGTTGAAAAACAACC

TGACAGCTTGCATTGCTGACTTTGGGTTGGCCTTAAAATTTGAGGCTGGC

AAGTCTGCAGGCGATACCCATGGACAGGTTGGTACCCGGAGGTACATGGC

TCCAGAGGTATTAGAGGGTGCTATAAACTTCCAAAGGGATGCATTTTTGA

GGATAGATATGTATGCCATGGGATTAGTCCTATGGGAACTGGCTTCTCGC

TGTACTGCTGCAGATGGACCTGTAGATGAATACATGTTGCCATTTGAGGA

GGAAATTGGCCAGCATCCATCTCTTGAAGACATGCAGGAAGTTGTTGTGC

ATAAAAAAAAGAGGCCTGTTTTAAGAGATTATTGGCAGAAACATGCTGGA

ATGGCAATGCTCTGTGAAACCATTGAAGAATGTTGGGATCACGACGCAGA

AGCCAGGTTATCAGCTGGATGTGTAGGTGAAAGAATTACCCAGATGCAGA

-continued
GACTAACAAATATTATTACCACAGAGGACATTGTAACAGTGGTCACAATG

GTGACAAATGTTGACTTTCCTCCCAAAGAATCTAGTCTATGA

The nucleic acid sequence encoding a human ActRIIa soluble (extracellular) polypeptide is as follows:

(SEQ ID NO: 5)
ATACTTGGTAGATCAGAAACTCAGGAGTGTCTTTTCTTTAATGCTAATTG

GGAAAAAGACAGAACCAATCAAACTGGTGTTGAACCGTGTTATGGTGACA

AAGATAAACGGCGGCATTGTTTTGCTACCTGGAAGAATATTTCTGGTTCC

ATTGAAATAGTGAAACAAGGTTGTTGGCTGGATGATATCAACTGCTATGA

CAGGACTGATTGTGTAGAAAAAAAAGACAGCCCTGAAGTATATTTTGTT

GCTGTGAGGGCAATATGTGTAATGAAAAGTTTTCTTATTTTCCAGAGATG

GAAGTCACACAGCCCACTTCAAATCCAGTTACACCTAAGCCACCC

In a specific embodiment, the invention relates to methods for treating or preventing breast cancer using soluble ActRIIa polypeptides. As described herein, the term "soluble ActRIIa polypeptide" generally refers to polypeptides comprising an extracellular domain of an ActRIIa protein. The term "soluble ActRIIa polypeptide," as used herein, includes any naturally occurring extracellular domain of an ActRIIa protein as well as any variants thereof (including mutants, fragments and peptidomimetic forms). An activin-binding ActRIIa polypeptide is one that retains the ability to bind to activin, including, for example, activin AA, AB, BB, or forms that include a C or E subunit. Optionally, an activin-binding ActRIIa polypeptide will bind to activin AA with a dissociation constant of 1 nM or less. The extracellular domain of an ActRIIa protein binds to activin and is generally soluble, and thus can be termed a soluble, activin-binding ActRIIa polypeptide. Examples of soluble, activin-binding ActRIIa polypeptides include the soluble polypeptide illustrated in SEQ ID NOs: 2, 3, 7, 12 and 13. SEQ ID NO:7 is referred to as ActRIIa-hFc, and is described further in the Examples. Other examples of soluble, activin-binding ActRIIa polypeptides comprise a signal sequence in addition to the extracellular domain of an ActRIIa protein, for example, the honey bee melitin leader sequence (SEQ ID NO: 8), the tissue plaminogen activator (TPA) leader (SEQ ID NO: 9) or the native ActRIIa leader (SEQ ID NO: 10). The ActRIIa-hFc polypeptide illustrated in SEQ ID NO: 13 uses a tPA leader.

Functionally active fragments of ActRIIa polypeptides can be obtained by screening polypeptides recombinantly produced from the corresponding fragment of the nucleic acid encoding an ActRIIa polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIa protein or signaling mediated by activin.

Functionally active variants of ActRIIa polypeptides can be obtained by screening libraries of modified polypeptides recombinantly produced from the corresponding mutagenized nucleic acids encoding an ActRIIa polypeptide. The variants can be produced and tested to identify those that can function as antagonists (inhibitors) of ActRIIa protein or signaling mediated, by activin. In certain embodiments, a functional variant of the ActRIIa polypeptides comprises an amino acid sequence that is at least 75% identical to an amino acid sequence selected from SEQ ID NOs: 2 or 3. In certain cases, the functional variant has an amino acid sequence at least 80%, 85%, 90%, 95%, 97%, 98%, 99% or 100% identical to an amino acid sequence selected from SEQ ID NOs: 2 or 3.

Functional variants may be generated by modifying the structure of an ActRIIa polypeptide for such purposes as enhancing therapeutic efficacy, or stability (e.g., ex vivo shelf life and resistance to proteolytic degradation in vivo). Such modified ActRIIa polypeptides when selected to retain activin binding, are considered functional equivalents of the naturally-occurring ActRIIa polypeptides. Modified ActRIIa polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIa polypeptide results in a functional homolog can be readily determined by assessing the ability of the variant ActRIIa polypeptide to produce a response in cells in a fashion similar to the wild-type ActRIIa polypeptide.

In certain embodiments, the present invention contemplates methods for treating or preventing breast cancer using ActRIIa polypeptides having specific mutations that alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the wild-type ActRIIa polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIa polypeptide is by chemical or enzymatic coupling of glycosides to the ActRIIa polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on an ActRIIa polypeptide may be accomplished chemically and/or enzymatically. Chemical deglycosylation may involve, for example, exposure of the ActRIIa polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on ActRIIa polypeptides can be achieved by the use of a variety of endo- and exo-glycosidases as described by Thotakura et al. (1987)

Meth. Enzymol. 138:350. The sequence of an ActRIIa polypeptide may be adjusted, as appropriate, depending on the type of expression system used, as mammalian, yeast, insect and plant cells may all introduce differing glycosylation patterns that can be affected by the amino acid sequence of the peptide. In general, ActRIIa proteins for use in humans may be expressed in a mammalian cell line that provides proper glycosylation, such as HEK293 or CHO cell lines, although other mammalian expression cell lines are expected to be useful as well.

This disclosure further contemplates methods of generating mutants, particularly sets of combinatorial mutants of an ActRIIa polypeptide, as well as truncation mutants; pools of combinatorial mutants are especially useful for identifying functional variant sequences. The purpose of screening such combinatorial libraries may be to generate, for example, ActRIIa polypeptide variants which bind to activin or other ligands. A variety of screening assays are provided below, and such assays may be used to evaluate variants. For example, an ActRIIa polypeptide variant may be screened for ability to bind to an ActRIIa ligand, to prevent binding of an ActRIIa ligand to an ActRIIa polypeptide or to interfere with signaling caused by an ActRIIa ligand.

The activity of an ActRIIa polypeptide or its variants may also be tested in a cell-based or in vivo assay. For example, the effect of an ActRIIa polypeptide variant on the proliferation or survival of cancer cells may be assessed. Cancer cells may refer to cells in a living subject that make up a solid tumor or to cells that have originated from a tumor and that have spread to other sites within a living subject (i.e., metastatic cells). Additionally, cancer cells may refer to cells obtained or derived from a tumor or cancerous growth and that are cultured in vitro. Cancer cells also encompass cell lines that may be cultivated in vitro or used in animal xenograft studies, for example. Cancer cells also refer to cells derived from metastatic cells through cell division following metastasis. The cells may be hormone-responsive (e.g., estrogen receptor positive) or hormone-independent (e.g., estrogen receptor negative). Cancer cell proliferation or survival may be assessed in the presence of one or more recombinant ActRIIa ligand proteins (e.g., activin), and cells may be transfected so as to produce an ActRIIa polypeptide and/or variants thereof, and optionally, an ActRIIa ligand. Likewise, an ActRIIa polypeptide may be administered to a mouse or other animal, and one or more measurements, such as tumor size, or the rate of cell proliferation or apoptosis relative to a control, may be assessed.

Combinatorially-derived variants can be generated which have a selective or generally increased potency relative to a naturally occurring ActRIIa polypeptide. Likewise, mutagenesis can give rise to variants which have intracellular half-lives dramatically different than the corresponding wild-type ActRIIa polypeptide. For example, the altered protein can be rendered either more stable or less stable to proteolytic degradation or other cellular processes which result in destruction of, or otherwise inactivation of a native ActRIIa polypeptide. Such variants, and the genes which encode them, can be utilized to alter ActRIIa polypeptide levels by modulating the half-life of the ActRIIa polypeptides. For instance, a short half-life can give rise to more transient biological effects and, when part of an inducible expression system, can allow tighter control of recombinant ActRIIa polypeptide levels within the cell. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIa polypeptide sequences. For instance, a mixture of synthetic oligonucleotides can be enzymatically ligated into gene sequences such that the degenerate set of potential ActRIIa polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIa polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell. Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIa polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIa polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, ActRIIa polypeptides useful in accordance with the methods described herein may further comprise post-translational modifications in addition to any that are naturally present in the ActRIIa polypeptides. Such modifications include, but are not limited to, acetylation, carboxylation, glycosylation, phosphorylation, lipidation, and acylation. As a result, the modified ActRIIa polypeptides may contain non-amino acid elements, such as polyethylene glycols, lipids, poly- or mono-saccharide, and phosphates. Effects of such non-amino acid elements on the functionality of an ActRIIa polypeptide may be tested as described herein for other ActRIIa polypeptide variants. When an ActRIIa polypeptide is produced in cells by cleaving a nascent form of the ActRIIa polypeptide, post-translational processing may also be important for correct folding and/or function of the protein. Different cells (such as CHO, HeLa, MDCK, WI38, NIH-3T3 or HEK293) have specific cellular machinery and characteristic mechanisms for such post-translational activities and may be chosen to ensure the correct modification and processing of the ActRIIa polypeptides.

In certain aspects, functional variants or modified forms of the ActRIIa polypeptides include fusion proteins having at least a portion of the ActRIIa polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$ (SEQ ID NO: 17)) fusion partners. As another example, a fusion domain may be selected so as to facilitate detection of the ActRIIa polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIa polypeptide is fused with a domain that stabilizes the ActRIIa polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function).

As a specific example, the present invention provides methods for treating or preventing breast cancer using a fusion protein comprising a soluble extracellular domain of ActRIIa fused to an Fc domain (e.g., SEQ ID NO: 6).

THTCPPCPAPELLGGPSVFLFPPKPKDTLMISRTPEVTCVVVD(A)VSHE

DPEVKFNWYVDGVEVHNAKTKPREEQYNSTYRVVSVLTVLHQDWLNGKEY

KCK(A)VSNKALPVPIEKTISKAKGQPREPQVYTLPPSREEMTKNQVSLT

CLVKGFYPSDIAVEWESNGQPENNYKTTPPVLDSDGPFFLYSKLTVDKSR

WQQGNVFSCSVMHEALHN(A)HYTQKSLSLSPGK*

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain. It is generally understood that an Fc domain may include smaller or larger portions of the constant region of an immunoglobulin, provided that the resulting "Fc domain" retains the ability to dimerize covalently through a disulfide linkage and forms a relative stable, soluble protein.

It is understood that different elements of the fusion proteins may be arranged in any manner that is consistent with the desired functionality. For example, an ActRIIa polypeptide may be placed C-terminal to a heterologous domain, or, alternatively, a heterologous domain may be placed C-terminal to an ActRIIa polypeptide. The ActRIIa polypeptide domain and the heterologous domain need not be adjacent in a fusion protein, and additional domains or amino acid sequences may be included C- or N-terminal to either domain or between the domains.

In certain embodiments, ActRIIa polypeptides useful in accordance with the methods described herein may contain one or more modifications that are capable of stabilizing the ActRIIa polypeptides. For example, such modifications enhance the in vitro half life of the ActRIIa polypeptides, enhance circulatory half life of the ActRIIa polypeptides or reducing proteolytic degradation of the ActRIIa polypeptides. Such stabilizing modifications include, but are not limited to, fusion proteins (including, for example, fusion proteins comprising an ActRIIa polypeptide and a stabilizer domain), modifications of a glycosylation site (including, for example, addition of a glycosylation site to an ActRIIa polypeptide), and modifications of carbohydrate moiety (including, for example, removal of carbohydrate moieties from an ActRIIa polypeptide). As used herein, the term "stabilizer domain" not only refers to a fusion domain (e.g., Fc) as in the case of fusion proteins, but also includes nonproteinaceous modifications such as a carbohydrate moiety, or nonproteinaceous moiety, such as polyethylene glycol.

In certain embodiments, the methods described herein utilize isolated and/or purified forms of the ActRIIa polypeptides, which are isolated from, or otherwise substantially free of, other proteins. ActRIIa polypeptides will generally be produced by expression from recombinant nucleic acids.

3. Nucleic Acids Encoding ActRIIa Polypeptides

Provided herein are isolated and/or recombinant nucleic acids encoding any of the ActRIIa polypeptides (e.g., soluble ActRIIa polypeptides), including fragments, functional variants and fusion proteins disclosed herein. For example, SEQ ID NO: 4 encodes the naturally occurring human ActRIIa precursor polypeptide, while SEQ ID NO: 5 encodes the processed extracellular domain of ActRIIa. The subject nucleic acids may be single-stranded or double stranded. Such nucleic acids may be DNA or RNA molecules. These nucleic acids may be used, for example, in methods for making ActRIIa polypeptides or as direct therapeutic agents (e.g., in a gene therapy approach).

In certain aspects, the subject nucleic acids encoding ActRIIa polypeptides are further understood to include nucleic acids that are variants of SEQ ID NO: 4 or 5. Variant nucleotide sequences include sequences that differ by one or more nucleotide substitutions, additions or deletions, such as allelic variants.

In certain embodiments, the invention provides methods for treating or preventing breast cancer using isolated or recombinant nucleic acid sequences that are at least 80%, 85%, 90%, 95%, 97%, 98%, 99% or 100% identical to SEQ ID NO: 4 or 5. One of ordinary skill in the art will appreciate that nucleic acid sequences complementary to SEQ ID NO: 4 or 5, and variants of SEQ ID NO: 4 or 5 are also within the scope of this invention. In further embodiments, the nucleic acid sequences described herein can be isolated, recombinant, and/or fused with a heterologous nucleotide sequence, or in a DNA library.

In other embodiments, nucleic acids useful in accordance with the methods described herein also include nucleotide sequences that hybridize under highly stringent conditions to the nucleotide sequence designated in SEQ ID NO: 4 or 5, complement sequence of SEQ ID NO: 4 or 5, or fragments thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the methods described herein utilize nucleic acids which hybridize under low stringency conditions of 6×SSC at room temperature followed by a wash at 2×SSC at room temperature.

Isolated nucleic acids which differ from the nucleic acids as set forth in SEQ ID NOs: 4 or 5 due to degeneracy in the genetic code are also contemplated for use in accordance with the methods described herein. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids described herein may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects, the methods described herein utilize an expression vector comprising a nucleotide sequence encoding an ActRIIa polypeptide that is operably linked to at least one regulatory sequence. Regulatory sequences are art-recognized and are selected to direct expression of the ActRIIa polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRIIa polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid described herein can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIa polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRIIa polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIa polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO: 4 or 5) for one or more of the subject ActRIIa polypeptides. The host cell may be any prokaryotic or eukaryotic cell. For example, an ActRIIa polypeptide described herein may be expressed in bacterial cells such as *E. coli,* insect cells (e.g., using a baculovirus expression system), yeast, or mammalian cells. Other suitable host cells are known to those skilled in the art.

Also provided herein are methods of producing the subject ActRIIa polypeptides. For example, a host cell transfected with an expression vector encoding an ActRIIa polypeptide can be cultured under appropriate conditions to allow expression of the ActRIIa polypeptide to occur. The ActRIIa polypeptide may be secreted and isolated from a mixture of cells and medium containing the ActRIIa polypeptide. Alternatively, the ActRIIa polypeptide may be retained cytoplasmically or in a membrane fraction and the cells harvested, lysed and the protein isolated. A cell culture includes host cells, media and other byproducts. Suitable media for cell culture are well known in the art. The subject ActRIIa polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIa polypeptides and affinity purification with an agent that binds to a domain fused to the ActRIIa polypeptide (e.g., a protein A column may be used to purify an ActRIIa-Fc fusion). In a preferred embodiment, the ActRIIa polypeptide is a fusion protein containing a domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. As demonstrated herein, ActRIIa-hFc protein was purified to a purity of >98% as determined by size exclusion chromatography and >95% as determined by SDS PAGE. This level of purity was sufficient to achieve desirable results in mice, rats and non-human primates.

In another embodiment, a fusion gene coding for a purification leader sequence, such as a poly-(His)/enterokinase cleavage site sequence at the N-terminus of the desired portion of the recombinant ActRIIa polypeptide, can allow purification of the expressed fusion protein by affinity chromatography using a $Ni^{2+}$ metal resin. The purification leader sequence can then be subsequently removed by treatment with enterokinase to provide the purified ActRIIa polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology,* eds. Ausubel et al., John Wiley & Sons: 1992).

4. Alternative Activin and ActRIIa Antagonists

The present disclosure relates to methods for treating or preventing breast cancer using antagonists of activin-ActRIIa signaling. Although soluble ActRIIa polypeptides, and particularly ActrIIa-Fc, are preferred antagonists, and although such antagonists may affect breast cancer cell growth or survival through a mechanism other than activin antagonism (e.g., activin inhibition may be an indicator of the tendency of an agent to inhibit the activities of a spectrum of molecules, including, perhaps, other members of the TGF-beta superfamily, and such collective inhibition may lead to the desired effect on breast cancer cell growth or survival), other types of activin-ActRIIa antagonists are expected to be useful, including anti-activin (e.g., activin $β_A$, $β_B$, $β_C$ and $β_E$) antibodies, anti-ActRIIa antibodies, antisense, RNAi or ribozyme nucleic acids that inhibit the production of ActRIIa and other inhibitors of activin or ActRIIa, particularly those that disrupt activin-ActRIIa binding. In certain embodiments, antagonists specific for activin B (e.g., anti-activin B antibodies) are useful in the methods of the present invention.

An antibody that is specifically reactive with an ActRIIa polypeptide (e.g., a soluble ActRIIa polypeptide) and which either binds competitively to ligand with the ActRIIa polypeptide or otherwise inhibits ActRIIa-mediated signaling may be used as an antagonist of ActRIIa polypeptide activities. Likewise, an antibody that is specifically reactive with an activin $\beta_A$, $\beta_B$, $\beta_C$ or $\beta_E$ polypeptide, or any heterodimer thereof, and which disrupts ActRIIa binding may be used as an antagonist.

By using immunogens derived from an ActRIIa polypeptide or an activin polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRIIa polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRIIa or activin polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRIIa polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ActRIIa polypeptide and monoclonal antibodies isolated from a culture comprising such hybridoma cells. Antibodies may also be generated by screening libraries (e.g., phage display libraries) of antibody variable domains or Fab fragments to identify binders that bind to the selected antigen (e.g., activins or ActRIIa). This in vitro approach is often useful with proteins that are highly conserved between mammals, particularly mice and humans.

The term "antibody" as used herein is intended to include whole antibodies, e.g., of any isotype (IgG, IgA, IgM, IgE, etc), and includes fragments or domains of immunoglobulins which are reactive with a selected antigen. Antibodies can be fragmented using conventional techniques and the fragments screened for utility and/or interaction with a specific epitope of interest. Thus, the term includes segments of proteolytically-cleaved or recombinanrtly-prepared portions of an antibody molecule that are capable of selectively reacting with a certain protein. Non-limiting examples of such proteolytic and/or recombinant fragments include Fab, F(ab')$_2$, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies. The term "recombinant antibody", means an antibody, or antigen binding domain of an immunoglobulin, expressed from a nucleic acid that has been constructed using the techniques of molecular biology, such as a humanized antibody or a fully human antibody developed from a single chain antibody. Single domain and single chain antibodies are also included within the term "recombinant antibody".

In certain embodiments, the methods described herein may utilize an antibody, such as, for example, a monoclonal antibody. Also provided are methods for generating novel antibodies. For example, a method for generating a monoclonal antibody that binds specifically to an ActRIIa polypeptide or activin polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ActRIIa polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody: antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ M or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore A B, Uppsala, Sweden), sandwich assays (e.g., the paramagnetic bead system of IGEN International, Inc., Gaithersburg, Md.), western blots, immunoprecipitation assays, and immunohistochemistry.

Examples of categories of nucleic acid compounds that are activin or ActRIIa antagonists include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100, or no more than 50, 35, 25, 22, 20, 18 or 15 nucleotides of the full-length ActRIIa nucleic acid sequence or activin $\beta_A$, $\beta_B$, $\beta_C$, or $\beta_E$ nucleic acid sequence. The region of complementarity will preferably be at least 8 nucleotides, and optionally about 18 to 35 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA or any other variation. The duplex portion of double stranded or single stranded "hairpin" RNAi construct will generally have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, the proliferation or survival of breast cancer cells or breast tumors.

5. Screening Assays

In certain aspects, the present invention relates to the use of ActRIIa polypeptides (e.g., soluble ActRIIa polypeptides) and activin polypeptides to identify compounds (agents) which are agonist or antagonists of the activin-ActRIIa signaling pathway. Compounds identified through this screening can be tested to assess their ability to modulate the growth or survival of cancer cells, particularly breast cancer cells, in vivo or in vitro. These compounds can be tested, for example, in animal models such as mouse xenograft models. One useful animal model is the murine MDA-MB231 breast cancer model; MDA-MB231 cells are hormone-independent and are prone to metastasize to the bone. Other animal models of breast cancer can be generated, for example, by implanting rat neuroblastoma cells (from which the neu oncogene was initially isolated), or neu-transformed NIH-3T3 cells into nude mice, essentially as described by Drebin et al. Proc. Nat. Acad. Sci. USA, 83: 9129-9133 (1986).

There are numerous approaches to screening for therapeutic agents for treating or preventing breast cancer by targeting activin and ActRIIa signaling. In certain embodiments, high-throughput screening of compounds can be carried out to identify agents that perturb activin or ActRIIa-mediated effects on a selected cell line. In certain embodiments, the assay is carried out to screen and identify compounds that specifically inhibit or reduce binding of an ActRIIa polypeptide to activin. Alternatively, the assay can be used to identify compounds that enhance binding of an ActRIIa polypeptide to activin. In a further embodiment, the compounds can be identified by their ability to interact with an activin or ActRIIa polypeptide.

A variety of assay formats will suffice and, in light of the present disclosure, those not expressly described herein will nevertheless be comprehended by one of ordinary skill in the art. As described herein, test compounds (agents) may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated herein include non-peptidyl organic molecules, peptides, polypeptides, peptidomimetics, sugars, hormones, and nucleic acid molecules. In a specific embodiment, the test agent is a small organic molecule having a molecular weight of less than about 2,000 Daltons.

Test compounds can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible cross-linkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIa polypeptide and activin.

Merely to illustrate, in an exemplary screening assay, the compound of interest is contacted with an isolated and purified ActRIIa polypeptide which is ordinarily capable of binding to activin. To the mixture of the compound and ActRIIa polypeptide is then added a composition containing an ActRIIa ligand. Detection and quantification of ActRIIa/activin complexes provides a means for determining the compound's efficacy at inhibiting (or potentiating) complex formation between the ActRIIa polypeptide and activin. The efficacy of the compound can be assessed by generating dose response curves from data obtained using various concentrations of the test compound. Moreover, a control assay can also be performed to provide a baseline for comparison. For example, in a control assay, isolated and purified activin is added to a composition containing the ActRIIa polypeptide, and the formation of ActRIIa/activin complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIa polypeptide and activin may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIa polypeptide or activin, by immunoassay, or by chromatographic detection.

In certain embodiments, fluorescence polarization assays and fluorescence resonance energy transfer (FRET) assays may be used for measuring, either directly or indirectly, the degree of interaction between an ActRIIa polypeptide and its binding protein. Other suitable modes of detection include, for example, those based on optical waveguides (PCT Publication WO 96/26432 and U.S. Pat. No. 5,677,196), surface plasmon resonance (SPR), surface charge sensors, and surface force sensors.

An interaction trap assay, also known as the "two hybrid assay," may also be used for identifying agents that disrupt or potentiate interaction between an ActRIIa polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, a reverse two hybrid system may be used to identify compounds (e.g., small molecules or peptides) that dissociate interactions between an ActRIIa polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, compounds are identified by their ability to interact with an ActRIIa or activin polypeptide described herein. The interaction between the compound and the ActRIIa or activin polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an activin or ActRIIa polypeptide. This may include a solid phase or fluid phase binding event. Alternatively, the gene encoding an activin or ActRIIa polypeptide can be transfected with a reporter system (e.g., β-galactosidase, luciferase, or green fluorescent protein) into a cell and screened against the library optionally by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using calorimetric or fluorescence or surface plasmon resonance.

6. Exemplary Therapeutic Uses

In certain embodiments, the present invention provides methods of treating or preventing breast cancer in an individual in need thereof by administering to the individual a therapeutically effective amount of an activin-ActRIIa antagonist, such as, for example, an ActRIIa polypeptide. These methods may be used for therapeutic as well as prophylactic treatment of humans, particularly females, who have a high risk for developing breast cancer. As every woman is at risk for developing breast cancer, a woman with a high risk for developing breast cancer is a woman whose risk factors confer a greater probability of developing the disease compared to the general population or the population of women within a certain age group. Exemplary risk factors include age, family history or genetic makeup, lifestyle habits such as exercise and diet, exposure to radiation or other cancer-causing agents, age at the time the first child was born, genetic changes, and weight gain after menopause.

As used herein, a therapeutic that "prevents" a disorder or condition refers to a compound that, in a statistical sample, reduces the occurrence of the disorder or condition in the treated sample relative to an untreated control sample, or delays the onset of one or more symptoms or characteristics of the disorder or condition relative to the untreated control sample. For example, preventing breast cancer may refer to the absence of new lesions following treatment, or the absence or delay of metastatic disease.

The term "treating breast cancer" refers to an improvement of one or more symptoms or characteristics of the disease relative to an untreated control or relative to the severity of disease prior to treatment. The term does not necessarily require that the patient receiving the treatment be cured or that the disease be completely eradicated from the patient. An agent that treats breast cancer may be an agent that reduces the severity of one or more symptoms or characteristics of the disease. It should be noted that tumor growth and progression is influenced by a variety of factors, including mediators of cell cycle progression and cell division and regulators of cell death, or apoptosis. Accordingly, treating breast cancer may involve a decrease in cancer cell proliferation or a decrease in the rate of cell division. Alternatively or additionally, treating breast cancer may involve a decrease in cancer cell survival, an increase in apoptosis or a diminished occurrence or severity of metastatic breast cancer, particularly metastatic breast cancer of the bone. Accordingly, in certain embodiments, treating breast cancer may involve both a decrease in cell division and an increase in cell death. Regardless of mechanism, the effectiveness of an agent in treating breast cancer may be determined by observable metrics, such as a lower number of cancer cells compared to a control (either due to decreased proliferation, increased apoptosis, or both), or a decrease in tumor size compared to a control. Therefore treating breast cancer or inhibiting tumor or cancer cell growth is intended to be neutral as to the mechanism by which such a change occurs. Both prevention and treatment may be discerned in the diagnosis provided by a physician or other health care provider and the analysis of the intended result of administration of the therapeutic agent.

When observing the effects of the subject antagonists on breast cancer progression in humans, an effect may be evaluated by a decrease or disappearance of measurable disease, and/or the absence of new lesions or the prevention of metastases. For example, activin-ActRIIa antagonists may significantly reduce or delay breast cancer progression in patients with both noninvasive and invasive breast cancer. In addition, the antagonists may prevent or reduce the risk of developing breast cancer in healthy women with risk factors for the disease. The antagonists may also reduce the risk of breast cancer recurrence in patients with a history of the disease.

Accordingly, activin-ActRIIa antagonists may be used to prevent or delay the onset of breast cancer in individuals considered to be at risk for developing the disease, and such antagonists may be used in selected patient populations. Examples of appropriate patient populations include patients with a family history of breast and ovarian cancer, such as female patients where a mother or sister has been diagnosed with the disease. Patients that have mutations in the BRCA1/2 genes or other genes shown to predispose women to breast and ovarian cancer are also included. In one embodiment, a patient considered to be at high risk for developing breast cancer but who has not been diagnosed with the disease is treated with an activin-ActRIIa antagonist. Such treatment may begin when the patient reaches the age of 30, 35, or 40, or when a female patient is not trying to conceive (i.e., the patient does not plan to nurse an infant) or has reached menopause. In particular, data presented herein demonstrates that activin-ActRIIa antagonists inhibit the metastatic spread of a breast cancer cell line introduced into the general circulation, demonstrating that such antagonists may be useful in preventing the metastases of breast tumors. Such compounds would be useful in treating any patient that has been diagnosed with breast cancer or suspected of having breast cancer. Additionally, patients that are considering having a preventative, or elective, mastectomy due to an elevated risk of developing a breast tumor may elect instead or in addition to take an activin-ActRIIa antagonist to diminish the risk of metastatic spread of undetected tumors.

Activin-ActRIIa antagonists disclosed herein, and particularly ActRIIa-Fc proteins, may be used to treat or prevent breast cancer in a patient, including patients with solid tumors as well as patients with metastatic cancer. Activin-ActRIIa antagonists may also be administered to human subjects with precancerous or benign lesions of the breast or with any abnormal proliferative lesions including typical hyperplasia, atypical hyperplasia, and noninvasive or in situ carcinoma. The antagonists of the present disclosure are also useful in the treatment or prevention of both hormone-dependent or hormone-responsive cancers (e.g., estrogen receptor positive cancers) and hormone-independent cancers (e.g., estrogen receptor negative or estrogen receptor mutant cancers). Activin-ActRIIa antagonists are also useful as therapeutic agents for cancers in which growth factors or oncogenes are activated (e.g., breast cancers in which c-erbB-2 (also known as HER-2/Neu) tyrosine kinase is expressed). Activin-ActRIIa antagonists may prove to be particularly useful in tumors that express elevated (relative to normal breast tissue-derived cells) levels of activin (e.g., A, AB or B) or elevated levels of ActRIIa or ActRIIb.

The present invention recognizes that the effectiveness of conventional cancer therapies (e.g., chemotherapy, radiation therapy, phototherapy, immunotherapy, and surgery) can be enhanced through the use of the subject antagonists. Accordingly, activin-ActRIIa antagonists may be used in combination therapies for the treatment, prevention, or management of breast cancer. The antagonists may be administered to patients in combination with radiation and/or surgical treatment as well as with cytotoxic chemotherapy and/or endocrine therapies. Such combination treatments may work synergistically and allow reduction of dosage of each of the individual treatments, thereby reducing the detrimental side effects exerted by each treatment at higher dosages. In other instances, malignancies that are refractory to a treatment may respond to a combination therapy of two or more different treatments. Accordingly, the disclosure relates to the administration of an activin-ActRIIa antagonist in combination with another conventional anti-neoplastic agent, either concomitantly or sequentially, in order to enhance the therapeutic effect of the anti-neoplastic agent or overcome cellular resistance to such anti-neoplastic agent.

Pharmaceutical compounds that may be used for combinatory anti-tumor therapy include, merely to illustrate: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic anti-tumor compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In certain embodiments, pharmaceutical compounds that may be used for combinatory therapy include anti-angiogenesis agents such as (1) inhibitors of release of "angiogenic molecules," such as bFGF (basic fibroblast growth factor); (2) neutralizers of angiogenic molecules, such as an anti-βbFGF antibodies; and (3) inhibitors of endothelial cell response to angiogenic stimuli, including collagenase inhibitor, basement membrane turnover inhibitors, angiostatic steroids, fungal-derived angiogenesis inhibitors, platelet factor 4, thrombospondin, arthritis drugs such as D-penicillamine and gold thiomalate, vitamin D3 analogs, alpha-interferon, and the like. For additional proposed inhibitors of angiogenesis, see Blood et al., Bioch. Biophys. Acta., 1032: 89-118 (1990), Moses et al., Science, 248:1408-1410 (1990), Ingber et al., Lab. Invest., 59:44-51 (1988), and U.S. Pat. Nos. 5,092,885, 5,112,946, 5,192,744, 5,202,352, and 6573256. In addition, there are a wide variety of compounds that can be used to inhibit angiogenesis, for example, peptides or agents that block the VEGF-mediated angiogenesis pathway, endostatin protein or derivatives, lysine binding fragments of angiostatin, melanin or melanin-promoting compounds, plasminogen fragments (e.g., Kringles 1-3 of plasminogen), tropoin subunits, antagonists of vitronectin αvβ3, peptides derived from Saposin B, antibiotics or analogs (e.g., tetracycline, or neomycin), dienogest-containing compositions, compounds comprising a MetAP-2 inhibitory core coupled to a peptide, the compound EM-138, chalcone and its analogs, and naaladase inhibitors. See, for example, U.S. Pat. Nos. 6,395,718, 6,462,075, 6,465,431, 6,475,784, 6,482,802, 6,482,810, 6,500,431, 6,500,924, 6,518,298, 6,521,439, 6,525,019, 6,538,103, 6,544,758, 6,544,947, 6,548,477, 6,559,126, and 6,569,845.

Depending on the nature of the combinatory therapy, administration of the therapeutic antagonists of the invention may be continued while the other therapy is being administered and/or thereafter. Administration of the antagonists described herein may be made in a single dose, or in multiple doses. In some instances, administration of the antagonists is commenced at least several days prior to the conventional therapy, while in other instances, administration is begun either immediately before or at the time of the administration of the conventional therapy.

7. Pharmaceutical Compositions

In certain embodiments, activin-ActRIIa antagonists described herein are formulated with a pharmaceutically acceptable carrier. For example, an ActRIIa polypeptide can be administered alone or as a component of a pharmaceutical formulation (therapeutic composition). The subject antagonists may be formulated for administration in any convenient way for use in human or veterinary medicine.

In certain embodiments, the methods for treating or preventing or breast cancer as described herein include administering the composition systemically, or locally as an implant or device. When administered, the therapeutic composition for use in this invention is, of course, in a pyrogen-free, physiologically acceptable form. Therapeutically useful agents other than the activin-ActRIIa antagonists which may also optionally be included in the composition as described above, may be administered simultaneously or sequentially with the subject antagonists in the methods of the invention.

Typically, activin-ActRIIa antagonists will be administered parentally. Pharmaceutical compositions suitable for parenteral administration may comprise one or more ActRIIa polypeptides in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., mammary epithelium). In certain embodiments, compositions described herein may include a matrix capable of delivering one or more therapeutic compounds (e.g., ActRIIa polypeptides) to a target tissue site (e.g., mammary epithelium), providing a structure for the developing tissue and optimally capable of being resorbed into the body. For example, the matrix may provide slow release of the ActRIIa polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, antagonists described herein can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An antagonist may also be administered as a bolus, electuary or paste.

In solid dosage forms for oral administration. (capsules, tablets, pills, dragees, powders, granules, and the like), one or more therapeutic antagonists may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Compositions useful in accordance with the methods described herein may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen suitable for treating or preventing breast cancer will be determined by the attending physician considering various factors which modify the action of the subject compounds of the invention (e.g., ActRIIa polypeptides). The various factors include, but are not limited to, the patient's age, sex, and diet, the severity of the disease, time of administration, and other clinical factors. The addition of other known growth factors to the final composition may also affect the dosage. Progress can be monitored by periodic assessment of various factors including but not limited to tumor size, stage, or histological grade, estrogen or progesterone receptor status, angioinvasion, and regional lymph node metastasis. The clinician may also monitor markers such as levels of the protein uPA/PAI1-high levels of uPA and PAI1 are associated with a high risk of metastasis—and Her-2 gene amplification and/or protein expression, which is also associated with metastasis (Weigelt et al. 2005 Nat. Rev. Cancer 5: 591-602). Gene expression profiling may also prove to be helpful in monitoring disease progression (van 't Veer et al. 2002 Nature 415: 530-536 and van de Vijver et al. 2002 N. Engl. J. Med. 347: 1999-2009).

In certain embodiments, the present invention also provides methods for treating or preventing breast cancer that involve gene therapy for the in vivo production of ActRIIa polypeptides. Such therapy would achieve its therapeutic effect by introduction of the ActRIIa polynucleotide sequences into cells or tissues involved in breast cancer, such as, for example, mammary epithelial cells. Delivery of ActRIIa polynucleotide sequences can be achieved using a recombinant expression vector such as a chimeric virus or a colloidal dispersion system. Preferred for therapeutic delivery of ActRIIa polynucleotide sequences is the use of targeted liposomes.

Various viral vectors which can be utilized for gene therapy as taught herein include adenovirus, herpes virus, vaccinia, or an RNA virus such as a retrovirus. The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRIIa polynucleotide.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRIIa polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain aspects and embodiments of the present invention, and are not intended to limit the invention.

Example 1

ActRIIa-Fc Fusion Proteins

Applicants constructed a soluble ActRIIa fusion protein that has the extracellular domain of human ActRIIa fused to a human or mouse Fc domain with a minimal linker in between. The constructs are referred to as ActRIIa-hFc and ActRIIa-mFc, respectively.

ActRIIa-hFc is shown below as purified from CHO cell lines (SEQ ID NO: 7):

```
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM
```

-continued
```
EVTQPTSNPVTPKPPTGGGTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPVPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK
```

The ActRIIa-hFc and ActRIIa-mFc proteins were expressed in CHO cell lines. Three different leader sequences were considered:
(i) Honey bee melitin (HBML): MKFLVNVALVFMVVYI-SYIYA (SEQ ID NO: 8),
(ii) Tissue Plasminogen Activator (TPA): MDAMKRGLC-CVLLLCGAVFVSP (SEQ ID NO: 9), and
(iii) Native: MGAAAKLAFAVFLISCSSGA (SEQ ID NO: 10).

The selected form employs the TPA leader and has the following unprocessed amino acid sequence:

```
                                      (SEQ ID NO: 13)
MDAMKRGLCCVLLLCGAVFVSPGAAILGRSETQECLFFNANWEKDRTNQT

GVEPCYGDKDKRRHCFATWKNISGSIEIVKQGCWLDDINCYDRTDCVEKK

DSPEVYFCCCEGNMCNEKFSYFPEMVTQPTSNPVTPKPPTGGGTHTCPPC

PAPELLGGPSVFLFPPKPKDTLMISRTPEVTCVVVDVSHEDPEVKFNWYV

DGVEVHNAKTKPREEQYNSTYRVVSVLTVLHQRTPEVTCVVVDVSHEDPE

VKFNWYVDGVEVHNAKTKPREEQYNSTYRVVSVLTVLHQDWLNGKEYKCK

VSNKALPVPIEKTISKAKGQPREPQVYTLPPSREEMTKNQVSLTCLVKGF

YPSDIAVEWESNGQPENNYKTTPPVLDSDGSFFLYSKLTVDKSRWQQGNV

FSCSVMHEALHNHYTQKSLSLSPGK
```

This polypeptide is encoded by the following nucleic acid sequence:

```
                                      (SEQ ID NO: 14)
ATGGATGCAATGAAGAGAGGGCTCTGCTGTGTGCTGCTGCTGTGTGGAGC

AGTCTTCGTTTCGCCCGGCGCCGCTATACTTGGTAGATCAGAAACTCAGG

AGTGTCTTTTTTTAATGCTAATTGGGAAAAAGACAGAACCAATCAAACTG

GTGTTGAACCGTGTTATGGTGACAAAGATAAACGGCGGCATTGTTTTGCT

ACCTGGAAGAATATTTCTGGTTCCATTGAATAGTGAAACAAGGTTGTTGG

CTGGATGATATCAACTGCTATGACAGGACTGATTGTGTAGAAAAAAAAGA

CAGCCCTGAAGTATATTTCTGTTGCTGTGAGGGCAATATGTGTAATGAAA

AGTTTTCTTATTTTCCGGAGATGGAAGTCACACAGCCCACTTCAAATCCA

GTTACACCTAAGCCACCCACCGGTGGTGGAACTCACACATGCCCACCGTG

CCCAGCACCTGAACTCCTGGGGGGACCGTCAGTCTTCCTCTTCCCCCCAA

AACCCAAGGACACCCTCATGATCTCCCGGACCCCTGAGGTCACATGCGTG

GTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGT

ACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCC
```

```
-continued
AGTCCCCATCGAGAAAACCATCTCCAAAGCCAAAGGGCAGCCCCGAGAAC

CACAGGTGTACACCCTGCCCCCATCCCGGGAGGAGATGACCAAGAACCAG

GTCAGCCTGACCTGCCTGGTCAAAGGCTTCTATCCCAGCGACATCGCCGT

GGAGTGGGAGAGCAATGGGCAGCCGGAGAACAACTACAAGACCACGCCTC

CCGTGCTGGACTCCGACGGCTCCTTCTTCCTCTATAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGAATTC
```

Both ActRIIa-hFc and ActRIIa-mFc were remarkably amenable to recombinant expression. As shown in FIG. 1, the protein was purified as a single, well-defined peak of protein. N-terminal sequencing revealed a single sequence of—ILGRSETQE (SEQ ID NO: 11). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIa-hFc protein was purified to a purity of >98% as determined by size exclusion chromatography and >95% as determined by SDS PAGE.

Figure 2:
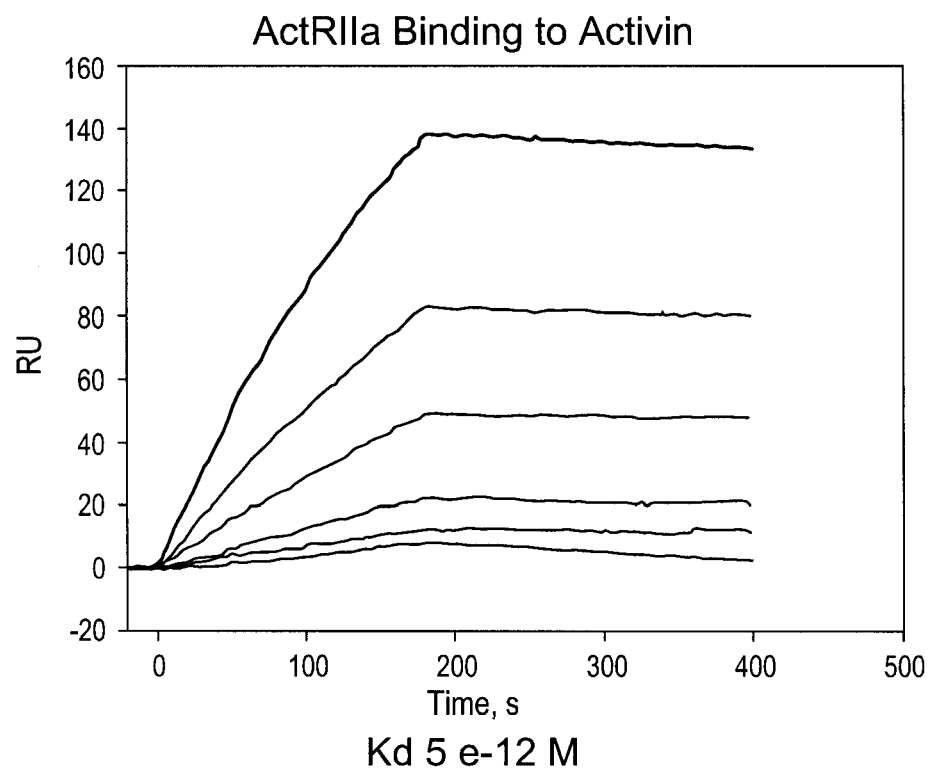
FIG. 2 shows the binding of ActRIIa-hFc to activin and GDF-11, as measured by BiaCore™ assay.
Figure 2:
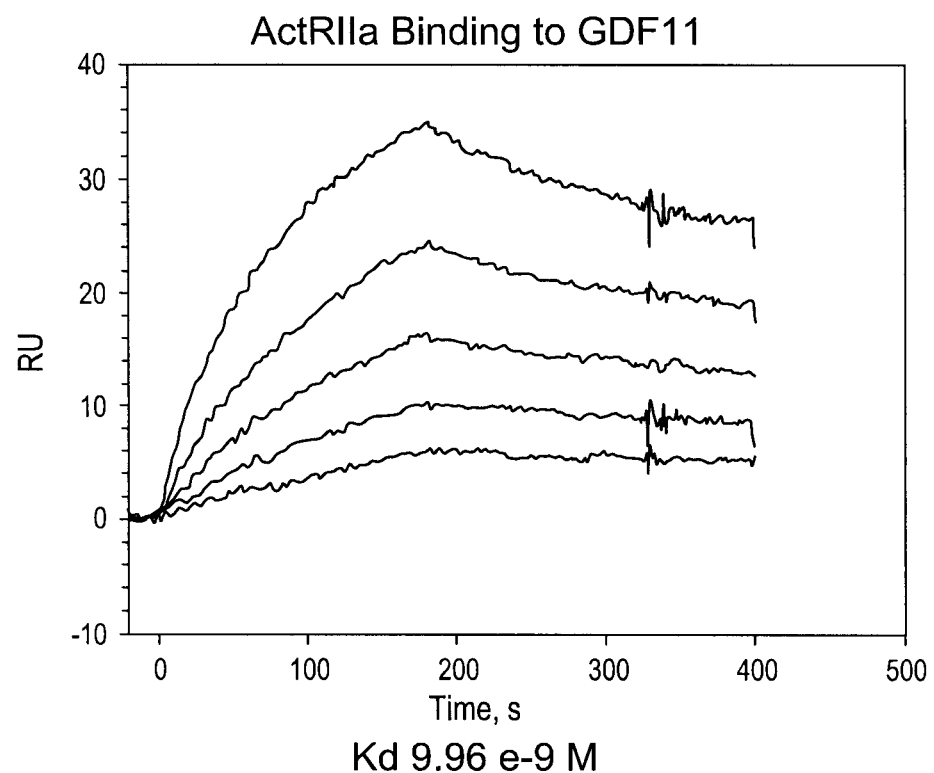

ActRIIa-hFc and ActRIIa-mFc showed a high affinity for ligands, particularly activin A. GDF-11 or Activin A ("ActA") were immobilized on a Biacore CM5 chip using standard amine coupling procedure. ActRIIa-hFc and ActRIIa-mFc proteins were loaded onto the system, and binding was measured. ActRIIa-hFc bound to activin with a dissociation constant ($K_D$) of $5 \times 10^{-12}$, and the protein bound to GDF11 with a $K_D$ of $9.96 \times 10^{-9}$. See FIG. 2. ActRIIa-mFc behaved similarly.

The ActRIIa-hFc was very stable in pharmacokinetic studies. Rats were dosed with 1 mg/kg, 3 mg/kg or 10 mg/kg of ActRIIa-hFc protein and plasma levels of the protein were measured at 24, 48, 72, 144 and 168 hours. In a separate study, rats were dosed at 1 mg/kg, 10 mg/kg or 30 mg/kg. In rats, ActRIIa-hFc had an 11-14 day serum half life and circulating levels of the drug were quite high after two weeks (11 µg/ml, 110 µg/ml or 304 µg/ml for initial administrations of 1 mg/kg, 10 mg/kg or 30 mg/kg, respectively.) In cynomolgus monkeys, the plasma half life was substantially greater than 14 days and circulating levels of the drug were 25 µg/ml, 304 µg/ml or 1440 µg/ml for initial administrations of 1 mg/kg, 10 mg/kg or 30 mg/kg, respectively.

Example 2

Characterization of an ActRIIa-hFc Protein

ActRIIa-hFc fusion protein was expressed in stably transfected CHO-DUKX B11 cells from a pAID4 vector (SV40 ori/enhancer, CMV promoter), using a tissue plasminogen leader sequence of SEQ ID NO:9. The protein, purified as described above in Example 1, had a sequence of SEQ ID NO:7. The Fc portion is a human IgG1 Fc sequence, as shown in SEQ ID NO:7. Sialic acid analysis showed that the protein contained, on average, between about 1.5 and 2.5 moles of sialic acid per molecule of ActRIIa-hFc fusion protein.

This purified protein showed a remarkably long serum half-life in all animals tested, including a half-life of 25-32 days in human patients (see Example 3, below). The CHO cell expressed material has a higher affinity for activin B ligand than that reported for an ActRIIa-hFc fusion protein expressed in human 293 cells (del Re et al., J Biol. Chem. 2004 Dec. 17; 279(51):53126-35.). Additionally, the use of the tPa leader sequence provided greater production than other leader sequences and, unlike ActRIIa-Fc expressed with a native leader, provided a highly pure N-terminal sequence. Use of the native leader sequence resulted in two major species of ActRIIa-Fc, each having a different N-terminal sequence.

Example 3

Human Clinical Trial

The protein described in Example 2 was administered to human patients in a randomized, double-blind, placebo-controlled study that was conducted to evaluate, primarily, the safety of the protein in healthy, postmenopausal women. Forty-eight subjects were randomized in cohorts of 6 to receive either a single dose of ActRIIa-hFc or placebo (5 active:1 placebo). Dose levels ranged from 0.01 to 3.0 mg/kg intravenously (IV) and 0.03 to 0.1 mg/kg subcutaneously (SC). All subjects were followed for 120 days. Subjects were excluded from study participation if they took medications affecting bone metabolism within 6 months of study entry. Safety evaluations were conducted following each cohort to determine dose escalation. In addition to pharmacokinetic (PK) analyses, the biologic activity of ActRIIa-hFc was also assessed by measurement of biochemical markers of bone formation and resorption, and FSH levels. No serious adverse events were reported in this study. Adverse events (AEs) were generally mild and transient. Preliminary analysis of AEs included headache, elevated laboratory values, cold symptoms, emesis or vomiting, intravenous infiltration, and hematoma at injection site.

PK analysis of ActRIIa-hFc displayed a linear profile with dose, and a mean half-life of approximately 25-32 days. The area-under-curve (AUC) for ActRIIa-hFc was linearly related to dose, and the absorption after SC dosing was essentially complete. These data indicate that SC is a desirable approach to dosing because it provides equivalent bioavailability and serum-half life for the drug while avoiding the spike in serum concentrations of drug associated with the first few days of IV dosing. ActRIIa-hFc caused a rapid, sustained dose-dependent increase in serum levels of bone-specific alkaline phosphatase (BAP), which is a marker for anabolic bone growth, and a dose-dependent decrease in C-terminal type 1 collagen telopeptide and tartrate-resistant acid phosphatase 5b levels, which are markers for bone resorption. Other markers, such as P1NP showed inconclusive results. BAP levels showed near saturating effects at the highest dosage of drug, indicating that half-maximal effects on this anabolic bone biomarker could be achieved at a dosage of 0.3 mg/kg, with increases ranging up to 3 mg/kg. Calculated as a relationship of pharmacodynamic effect to AUC for drug, the EC50 is 51,465 (day*ng/ml). These bone biomarker changes were sustained for approximately 120 days at the highest dose levels tested. There was also a dose-dependent decrease in serum FSH levels consistent with inhibition of activin.

A single dose of ActRIIa-hFc given to healthy postmenopausal women was safe and well-tolerated for the range of dose levels tested. The prolonged PK and pharmacodynamic effects suggest that intermittent dosing would be appropriate for future studies. For example, dosing on the basis of serum half-life could be performed on a monthly basis, or on the order of once every two, three, four, five or six weeks. Additionally, because the pharmacodynamic effect extends far beyond the serum residence of the drug, dosing could be performed on the basis of the pharmacodynamic effect, meaning that dosing every three months or every two, three, four, five, six or even twelve months may be effective to produce the desired effect in patients. This clinical trial demonstrates that, in humans, ActRIIa-hFc is an osteoanabolic agent with biological evidence of both an increase in bone formation and a decrease in bone resorption.

Example 4

ActRIIa-Fc Ameliorates or Prevents Bone Loss Caused by Breast Cancer Metastases

It is estimated that 65 to 75 percent of breast cancers metastasize to the bone, causing substantial damage to the bone structure, increasing fracture risk and causing pain and other side effects. We tested the effects of ActRIIa-Fc in a mouse model of breast cancer that has metastasized to the bone.

A subline of the human breast cancer cell line MDA-MB-231 (clone 2287, Kang et al. Cancer Cell 2003, vol 3:537-549) was cultured in vitro and cells harvested at a density of $5 \times 10^6$ cells/ml. MDA-MB-231 is a cell line that is highly competent for seeding into bone and causing bone damage similar to that caused by bone metastases. 10 µl of cells were injected into the tibia of 6 week old female athymic nude mice on study day 0. On study day 10 mice received ActRIIa-mFc (10 mg/kg/twice weekly/subcutaneous) (n=8) or PBS vehicle (n=7). Disease progression was assessed by changes in bone mineral density using dual energy x-ray absorptiometry (PIXIMus) at weekly intervals. Mice were treated with ActRIIa-mFc for 4 weeks and then sacrificed and tibae (both tumor injected and untumored) were collected from each animal. Tibiae were then processed and prepared for microcomputed tomography (microCT) and histololgical analysis.

Intratibial injection of MDA-MB-231 cells into athymic nude mice promoted the development of osteolytic bone lesions in the injected tibia compared to the contralateral leg. MicroCT analysis of the proximal tibia, demonstrated a 62%, reduction in cancellous bone volume in the MDA-MB-231 bearing tibiae compared to the untumored tibia in PBS vehicle treated mice. ActRIIa-mFc treatment led to an increase of 70% or 147% in the naïve or tumor bearing tibia respectively compared to vehicle (P<0.01 for both). The tumor bearing tibiae of ActRIIa-mFc treated mice had a similar cancellous bone density as the naïve tibiae of the VEH treated mice (p=0.39).

Thus, ActRIIa-mFc is able to eliminate the bone damage associated with the presence of breast tumor cells in the bone.

Example 5

ActRIIa-Fc Reduces Breast Cancer Metastases and Promotes Survival

As a model of metastatic disease, MDA-MB-231 cells can be introduced into mice by intracardiac injection. Cells injected into the left ventricle will migrate through the bloodstream and form metastatic lesions at distal sites. A derivative cell line MDA-MB-231-luc-D3H2LN (Caliper Life Sciences) is a luciferase expressing cell line that allows for non-invasive monitoring of metastatic tumor formation using biophotonic imaging technology (Caliper Life Sciences). This model was used to evaluate the potential of ActRIIa-mFc to diminish the formation of metastatic breast cancer lesions.

MDA-MB-231-luc-D3H2LN cells were introduced by intracardiac injection into twenty-six athymic nude mice. Fourteen of the mice were treated with vehicle (Phosphate buffered saline-PBS) and twelve were treated with ActRIIa-mFc (10 mg/kg, twice weekly, subcutaneous injection) starting two weeks prior to tumor administration and continuing through the course of the study. An additional nine mice were mock injected with cells and treated with ActRIIa-mFc. Mice were periodically anaesthetized and visualized for bioluminescent emission to detect the formation of metastatic progression.

Figure 3:
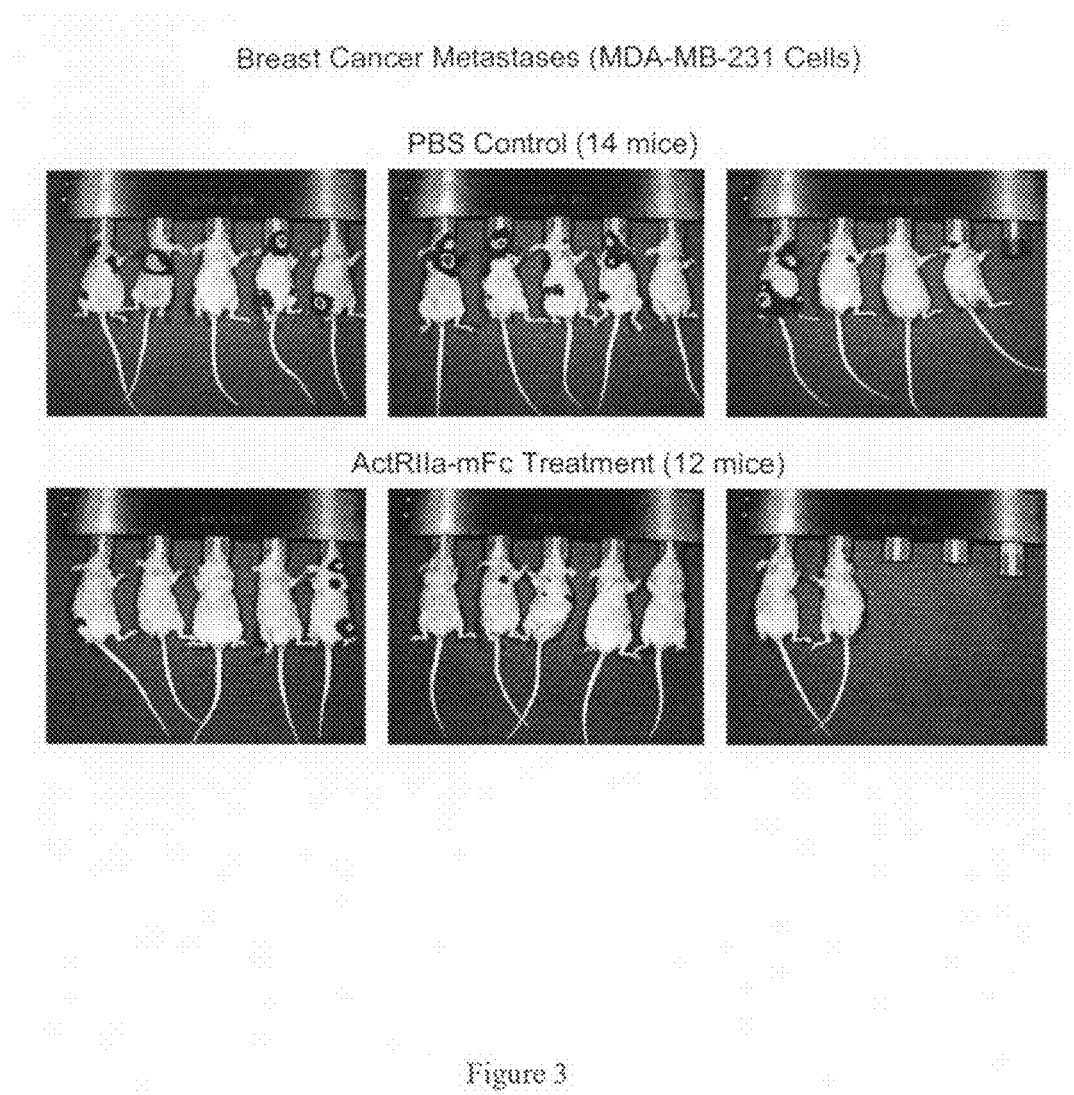
FIG. 3 shows that ActRIIa-mFc treatment greatly reduces the formation of metastatic lesions in a mouse model of metastatic breast cancer. Mice were visualized non-invasively (anaesthetized, fluorescent imaging) five weeks after intracardiac injection of luciferase expressing MDA-MB-231 breast cancer cells. 12/14 vehicle treated mice show visible metastatic lesions, while only 4/12 ActRIIa-mFc treated mice show visible lesions.

The ActRIIa-mFc treatment group showed substantially reduced development of metastatic lesions. By week five, twelve of fourteen vehicle treated mice showed multiple, strong fluorescent signals indicative of metastatic spread, while only four of twelve ActRIIa-mFc treated mice showed similar lesions (FIG. 3). A quantitation of fluorescence intensity showed a roughly ten-fold decrease in fluorescence signal in the treated mice.

Moreover, the ActRIIa-mFc treatment markedly increased survival of the mice. By study day forty, all (14/14) of the vehicle treated mice had died or had been euthanized (according to standard procedures for humane treatment of study animals), while only two (2/12) of the ActRIIa-mFc treated mice had died or had been euthanized. By day forty-five, 3/12 ActRIIa-mFc treated mice had died or had been euthanized, and none of the mock injected mice had died.

Therefore, ActRIIa-mFc treatment causes a substantial decrease in the formation of metastatic lesions, and promotes survival, in this model of metastatic breast cancer. These data indicate that ActRIIa-Fc may be used to treat breast cancer in human patients, particularly in conjunction with therapies, such as surgery, hormone therapy or traditional chemotherapy which target the primary tumor.

Example 6

Alternative ActRIIa-Fc Proteins

A variety of ActRIIa variants that may be used according to the methods described herein are described in the International Patent Application published as WO2006/012627 (see e.g., pp. 55-60), incorporated herein by reference in its entirety. An alternative construct may have a deletion of the C-terminal tail (the final 15 amino acids of the extracellular domain of ActRIIa. The sequence for such a construct is presented below (Fc portion underlined) (SEQ ID NO: 12):

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

TGGGTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPVPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for treating or preventing estrogen receptor-negative breast cancer in a human patient, the method comprising administering to a patient in need thereof an effective amount of an ActRIIa-Fc fusion protein, wherein the ActRIIa-Fc fusion protein comprises a polypeptide comprising an amino acid sequence that is at least 95% identical to SEQ ID NO:2, and wherein the ActRIIa-Fc fusion protein binds to activin A.

2. The method of claim 1, wherein the ActRIIa-Fc fusion protein has one or more of the following characteristics:
   a. binds to activin A with a $K_D$ of at least $10^{-7}$ M; and
   b. inhibits ActRIIa signaling in a cell.

3. The method of claim 2, wherein said ActRIIa-Fc fusion protein comprises one or more modified amino acid residues selected from: a glycosylated amino acid, a PEGylated amino acid, a farnesylated amino acid, an acetylated amino acid, a biotinylated amino acid, and an amino acid conjugated to a lipid moiety.

4. The method of claim 1, wherein the ActRIIa-Fc fusion protein comprises the amino acid sequence of SEQ ID NO:2.

5. The method of claim 1, wherein the ActRIIa-Fc fusion protein is a dimer formed of two polypeptides that each comprise an amino acid sequence that is at least 95% identical to the amino acid sequence of SEQ ID NO:2, and wherein the ActRIIa-Fc fusion protein comprises three or more sialic acid moieties.

6. The method of claim 5, wherein the ActRIIa-Fc fusion protein comprises the amino acid sequence of SEQ ID NO:2.

7. The method of claim 6, wherein the ActRIIa-Fc fusion protein comprises from three to five sialic acid moieties.

8. The method of claim 7, wherein the method causes less than a 10% increase in the patient's skeletal muscle mass.

9. The method of claim 7, wherein the ActRIIa-Fc fusion protein is administered so as to reach a serum concentration of the fusion protein in the patient of at least 0.2 mg/kg.

10. The method of claim 7, wherein the ActRIIa-Fc fusion protein comprises an amino acid sequence that is at least 95% identical to SEQ ID NO:7.

11. The method of claim 7, wherein the ActRIIa-Fc fusion protein has a serum half-life of between 15 and 40 days in normal, healthy humans.

12. The method of claim 7, wherein the ActRIIa-Fc fusion protein is administered to the patient no more frequently than once per week.

13. The method of claim 7, wherein the ActRIIa-Fc fusion protein is administered to the patient no more frequently than once per month.

14. The method of claim 7, wherein the ActRIIa-Fc fusion protein is administered to the patient no more frequently than once per three months.

15. The method of claim 1, further comprising administering a radiation therapy, endocrine therapy or cytotoxic agent to the human patient.

16. The method of claim 1, wherein the human patient is a female with one or more risk factors for breast cancer.

17. The method of claim 1, wherein the ActRIIa-Fc fusion protein comprises an amino acid sequence that is at least 95% identical to SEQ ID NO:7.

18. The method of claim 17, wherein the ActRIIa-Fc fusion protein comprises the amino acid sequence of SEQ ID NO:7.

19. The method of claim 10, wherein the ActRIIa-Fc fusion protein comprises the amino acid sequence of SEQ ID NO:7.

20. The method of claim 1, wherein the patient is at risk for developing metastatic cancer.

21. The method of claim 1, wherein the patient has a primary breast cancer tumor or proliferative lesion of the breast, and wherein the ActRIIa-Fc fusion protein is administered to the patient prior to the development of metastatic lesions.

22. The method of claim 1, wherein the patient has a primary breast cancer tumor or proliferative lesion of the breast, and wherein the ActRIIa-Fc fusion protein is administered to the patient prior to metastatic spread of cancer cells to the bone.

23. The method of claim 1, wherein the method is for treating estrogen receptor-negative breast cancer in a human patient.

24. The method of claim 23, wherein the ActRIIa-Fc fusion protein comprises a polypeptide comprising the amino acid sequence of SEQ ID NO:2.

25. The method of claim 23, wherein the ActRIIa-Fc fusion protein comprises a polypeptide comprising an amino acid sequence that is at least 95% identical to SEQ ID NO:7.

26. The method of claim 23, wherein the ActRIIa-Fc fusion protein comprises a polypeptide comprising the amino acid sequence of SEQ ID NO:7.

27. The method of claim 23, wherein the ActRIIa-Fc fusion protein is a dimer comprising two polypeptides that each comprise an amino acid sequence that is at least 95% identical to the amino acid sequence of SEQ ID NO:7.

28. The method of claim 23, wherein the ActRIIa-Fc fusion protein is a dimer comprising two polypeptides that each comprise the amino acid sequence of SEQ ID NO:7.

29. The method of claim 1, wherein the method is for preventing estrogen receptor-negative breast cancer in a human patient.

30. The method of claim 29, wherein the ActRIIa-Fc fusion protein comprises a polypeptide comprising the amino acid sequence of SEQ ID NO:2.

31. The method of claim 29, wherein the ActRIIa-Fc fusion protein comprises a polypeptide comprising an amino acid sequence that is at least 95% identical to SEQ ID NO:7.

32. The method of claim 29, wherein the ActRIIa-Fc fusion protein comprises a polypeptide comprising the amino acid sequence of SEQ ID NO:7.

33. The method of claim 29, wherein the ActRIIa-Fc fusion protein is a dimer comprising two polypeptides that each comprise an amino acid sequence that is at least 95% identical to the amino acid sequence of SEQ ID NO:7.

34. The method of claim 29, wherein the ActRIIa-Fc fusion protein is a dimer comprising two polypeptides that each comprise the amino acid sequence of SEQ ID NO:7.

* * * * *

SEQUENCE LISTING

```
<160> NUMBER OF SEQ ID NOS: 17

<210> SEQ ID NO 1
<211> LENGTH: 513
<212> TYPE: PRT
<213> ORGANISM: Homo sapiens

<400> SEQUENCE: 1

Met Gly Ala Ala Ala Lys Leu Ala Phe Ala Val Phe Leu Ile Ser Cys
 1               5                  10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
```

```
            305                 310                 315                 320
Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
                340                 345                 350

Ala Gly Asp Thr His Gly Gln Val Gly Thr Arg Arg Tyr Met Ala Pro
                355                 360                 365

Glu Val Leu Glu Gly Ala Ile Asn Phe Gln Arg Asp Ala Phe Leu Arg
            370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
                420                 425                 430

Val His Lys Lys Lys Arg Pro Val Leu Arg Asp Tyr Trp Gln Lys His
            435                 440                 445

Ala Gly Met Ala Met Leu Cys Glu Thr Ile Glu Glu Cys Trp Asp His
            450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
                500                 505                 510

Leu

<210> SEQ ID NO 2
<211> LENGTH: 115
<212> TYPE: PRT
<213> ORGANISM: Homo sapiens

<400> SEQUENCE: 2

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
                20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
                100                 105                 110

Lys Pro Pro
        115

<210> SEQ ID NO 3
<211> LENGTH: 100
<212> TYPE: PRT
<213> ORGANISM: Homo sapiens

<400> SEQUENCE: 3
```

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
            85                  90                  95

Phe Pro Glu Met
            100

<210> SEQ ID NO 4
<211> LENGTH: 1542
<212> TYPE: DNA
<213> ORGANISM: Homo sapiens

<400> SEQUENCE: 4
atgggagctg ctgcaaagtt ggcgtttgcc gtctttctta tctcctgttc ttcaggtgct      60
atacttggta gatcagaaac tcaggagtgt ctttctttta tgctaattg gaaaaagac      120 agaaccaatc aaactggtgt tgaaccgtgt tatggtgaca agataaacg gcggcattgt      180 tttgctacct ggaagaatat ttctggttcc attgaaatag tgaaacaagg ttgttggctg      240
gatgatatca actgctatga caggactgat tgtgtagaaa aaaagacag ccctgaagta      300 tattttgtt gctgtgaggg caatatgtgt aatgaaaagt tttcttattt tccagagatg      360
gaagtcacac agcccacttc aaatccagtt acacctaagc caccctata caacatcctg      420 ctctattcct tggtgccact tatgttaatt gcggggattg tcatttgtgc atttgggtg      480 tacaggcatc acaagatggc ctaccctcct gtacttgttc aactcaaga cccaggacca      540 cccccacctt ctccattact agggttgaaa ccactgcagt tattagaagt gaaagcaagg      600
ggaagatttg gttgtgtctg gaaagcccag ttgcttaacg aatatgtggc tgtcaaaata      660
tttccaatac aggacaaaca gtcatggcaa aatgaatacg aagtctacag tttgcctgga      720
atgaagcatg agaacatatt acagttcatt ggtgcagaaa acgaggcac cagtgttgat      780 gtggatcttt ggctgatcac agcatttcat gaaaagggtt cactatcaga ctttcttaag      840
gctaatgtgg tctcttggaa tgaactgtgt catattgcag aaaccatggc tagaggattg      900
gcatatttac atgaggatat acctggccta aaagatggcc acaaacctgc catatctcac      960
agggacatca aaagtaaaaa tgtgctgttg aaaaacaacc tgacagcttg cattgctgac     1020
tttgggttgg ccttaaaatt tgaggctggc aagtctgcag cgatacccca tggacaggtt     1080
ggtacccgga ggtacatggc tccagaggta ttagagggtg ctataaactt ccaaagggat     1140 gcattttga ggatagatat gtatgccatg ggattagtcc tatgggaact ggcttctcgc     1200
tgtactgctg cagatggacc tgtagatgaa tacatgttgc catttgagga ggaaattggc     1260
cagcatccat ctcttgaaga catgcaggaa gttgttgtgc ataaaaaaa gaggcctgtt     1320 ttaagagatt attggcagaa acatgctgga atgcaatgc tctgtgaaac cattgaagaa     1380
tgttgggatc acgacgcaga agccaggtta tcagctggat gtgtaggtga agaattacc     1440 cagatgcaga gactaacaaa tattattacc acagaggaca ttgtaacagt ggtcacaatg     1500

```
gtgacaaatg ttgactttcc tcccaaagaa tctagtctat ga            1542
```

```
<210> SEQ ID NO 5
<211> LENGTH: 345
<212> TYPE: DNA
<213> ORGANISM: Homo sapiens

<400> SEQUENCE: 5
```

```
atacttggta gatcagaaac tcaggagtgt cttttcttta atgctaattg ggaaaaagac     60
agaaccaatc aaactggtgt tgaaccgtgt tatggtgaca agataaacg gcggcattgt    120 tttgctacct ggaagaatat ttctggttcc attgaaatag tgaaacaagg ttgttggctg    180
gatgatatca actgctatga caggactgat tgtgtagaaa aaaagacag ccctgaagta    240 tattttgtt gctgtgaggg caatatgtgt aatgaaaagt tttcttattt tccagagatg    300
gaagtcacac agcccacttc aaatccagtt acacctaagc caccc                    345
```

```
<210> SEQ ID NO 6
<211> LENGTH: 225
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (43)
<223> OTHER INFORMATION: Asp or Ala
<220> FEATURE:
<221> NAME/KEY: MOD_RES
<222> LOCATION: (100)
<223> OTHER INFORMATION: Lys or Ala
<220> FEATURE:
<221> NAME/KEY: MOD_RES
<222> LOCATION: (212)
<223> OTHER INFORMATION: Asn or Ala

<400> SEQUENCE: 6
```

```
Thr His Thr Cys Pro Pro Cys Pro Ala Pro Glu Leu Leu Gly Gly Pro
  1               5                  10                  15

Ser Val Phe Leu Phe Pro Pro Lys Pro Lys Asp Thr Leu Met Ile Ser
             20                  25                  30

Arg Thr Pro Glu Val Thr Cys Val Val Val Xaa Val Ser His Glu Asp
         35                  40                  45

Pro Glu Val Lys Phe Asn Trp Tyr Val Asp Gly Val Glu Val His Asn
     50                  55                  60

Ala Lys Thr Lys Pro Arg Glu Glu Gln Tyr Asn Ser Thr Tyr Arg Val
 65                  70                  75                  80

Val Ser Val Leu Thr Val Leu His Gln Asp Trp Leu Asn Gly Lys Glu
                 85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175
```

```
Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
        210                 215                 220

Lys
225

<210> SEQ ID NO 7
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300
```

-continued

```
Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
            325                 330                 335

Ser Leu Ser Leu Ser Pro Gly Lys
            340

<210> SEQ ID NO 8
<211> LENGTH: 21
<212> TYPE: PRT
<213> ORGANISM: Apis mellifera

<400> SEQUENCE: 8

Met Lys Phe Leu Val Asn Val Ala Leu Val Phe Met Val Val Tyr Ile
1               5                   10                  15

Ser Tyr Ile Tyr Ala
            20

<210> SEQ ID NO 9
<211> LENGTH: 22
<212> TYPE: PRT
<213> ORGANISM: Unknown
<220> FEATURE:
<223> OTHER INFORMATION: Description of Unknown Organism: Tissue
      Plasminogen Activator peptide

<400> SEQUENCE: 9

Met Asp Ala Met Lys Arg Gly Leu Cys Cys Val Leu Leu Leu Cys Gly
1               5                   10                  15

Ala Val Phe Val Ser Pro
            20

<210> SEQ ID NO 10
<211> LENGTH: 20
<212> TYPE: PRT
<213> ORGANISM: Unknown
<220> FEATURE:
<223> OTHER INFORMATION: Description of Unknown Organism: Native peptide

<400> SEQUENCE: 10

Met Gly Ala Ala Ala Lys Leu Ala Phe Ala Val Phe Leu Ile Ser Cys
1               5                   10                  15

Ser Ser Gly Ala
            20

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Leu Gly Arg Ser Glu Thr Gln Glu
1               5

<210> SEQ ID NO 12
<211> LENGTH: 329
<212> TYPE: PRT
<213> ORGANISM: Artificial Sequence
<220> FEATURE:
<223> OTHER INFORMATION: Description of Artificial Sequence: Synthetic
      construct
```

<400> SEQUENCE: 12

```
Ile Leu Gly Arg Ser Glu Thr Gln Glu Cys Leu Phe Phe Asn Ala Asn
 1               5                  10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Thr Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Val Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 13
<211> LENGTH: 369
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 13

Met Asp Ala Met Lys Arg Gly Leu Cys Cys Val Leu Leu Leu Cys Gly
 1               5                  10                  15
```

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Val Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 14
<211> LENGTH: 1114
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 14

```
atggatgcaa tgaagagagg gctctgctgt gtgctgctgc tgtgtggagc agtcttcgtt      60
tcgcccggcg ccgctatact tggtagatca gaaactcagg agtgtctttt tttaatgcta    120
attgggaaaa agacagaacc aatcaaactg gtgttgaacc gtgttatggt gacaaagata    180
aacggcggca ttgttttgct acctggaaga atatttctgg ttccattgaa tagtgaaaca    240
aggttgttgg ctggatgata tcaactgcta tgacaggact gattgtgtag aaaaaaaaga    300
cagccctgaa gtatatttct gttgctgtga gggcaatatg tgtaatgaaa agttttctta    360 tttccggag atggaagtca cacagcccac ttcaaatcca gttacaccta agccacccac    420
cggtggtgga actcacacat gcccaccgtg cccagcacct gaactcctgg ggggaccgtc    480
agtcttcctc ttccccccaa aacccaagga caccctcatg atctcccgga cccctgaggt    540
cacatgcgtg gtggtggacg tgagccacga agaccctgag gtcaagttca actggtacgt    600
ggacggcgtg gaggtgcata atgccaagac aaagccgcgg gaggagcagt acaacagcac    660
gtaccgtgtg gtcagcgtcc tcaccgtcct gcaccaggac tggctgaatg caaggagta    720 caagtgcaag gtctccaaca aagccctccc agtccccatc gagaaaacca tctccaaagc    780
caaagggcag ccccgagaac cacaggtgta caccctgccc ccatcccggg aggagatgac    840
caagaaccag gtcagcctga cctgcctggt caaaggcttc tatcccagcg acatcgccgt    900
ggagtgggag agcaatgggc agccggagaa caactacaag accacgcctc ccgtgctgga    960
ctccgacggc tccttcttcc tctatagcaa gctcaccgtg gacaagagca ggtggcagca   1020
ggggaacgtc ttctcatgct ccgtgatgca tgaggctctg cacaaccact acacgcagaa   1080
gagcctctcc ctgtctccgg gtaaatgaga attc                                1114
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Gly Gly Gly Gly
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gly Gly Gly Gly
 1               5

<210> SEQ ID NO 17
<211> LENGTH: 6
<212> TYPE: PRT

```
<213> ORGANISM: Artificial Sequence
<220> FEATURE:
<223> OTHER INFORMATION: Description of Artificial Sequence: Synthetic
      6xHis tag

<400> SEQUENCE: 17

His His His His His His
  1               5
```